United States Patent
Ilan et al.

(10) Patent No.: US 9,907,810 B1
(45) Date of Patent: Mar. 6, 2018

(54) GLUCOCEREBROSIDE TREATMENT OF LIVER DISORDERS

(71) Applicant: Enzo Therapeutics, Inc., New York, NY (US)

(72) Inventors: Yaron Ilan, Jerusalem (IL); Maya Margalit, Abu Gosh (IL)

(73) Assignee: Enzo Therapeutics, Inc., New York, NY (US)

( * ) Notice: Subject to any disclaimer, the term of this patent is extended or adjusted under 35 U.S.C. 154(b) by 0 days.

(21) Appl. No.: 15/647,431

(22) Filed: Jul. 12, 2017

Related U.S. Application Data

(63) Continuation of application No. 11/378,941, filed on Mar. 17, 2006, now Pat. No. 9,744,185, which is a continuation-in-part of application No. 10/675,980, filed on Sep. 30, 2003, now Pat. No. 9,717,754, which is a continuation-in-part of application No. 10/375,906, filed on Feb. 27, 2003, now abandoned.

(51) Int. Cl.
- *A61K 31/70* (2006.01)
- *A61K 31/7032* (2006.01)
- *A61K 31/739* (2006.01)
- *A61K 38/17* (2006.01)

(52) U.S. Cl.
CPC ........ *A61K 31/7032* (2013.01); *A61K 31/739* (2013.01); *A61K 38/1709* (2013.01)

(58) Field of Classification Search
None
See application file for complete search history.

(56) References Cited

U.S. PATENT DOCUMENTS

| | | |
|---|---|---|
| 4,598,051 A | 7/1986 | Papahadjopoulos et al. |
| 5,101,026 A | 3/1992 | Ogawa et al. |
| 5,709,879 A | 1/1998 | Barchfeld et al. |
| 5,747,463 A | 5/1998 | Marinier et al. |
| 5,861,520 A | 1/1999 | Ogawa et al. |
| 5,869,048 A | 2/1999 | Das |
| 5,942,237 A | 8/1999 | Gizurarson et al. |
| 6,043,339 A | 3/2000 | Lin et al. |
| 6,280,774 B1 | 8/2001 | Rang et al. |
| 6,355,626 B1 | 3/2002 | Panettieri et al. |
| 6,610,835 B1 | 8/2003 | Liotta et al. |
| 6,756,208 B2 | 6/2004 | Griffin |
| 6,756,504 B2 | 6/2004 | Dagan et al. |
| 7,897,560 B2 | 3/2011 | Ilan et al. |
| 7,897,580 B2 | 3/2011 | Ilan et al. |
| 2002/0141977 A1 | 10/2002 | Collins et al. |
| 2003/0157135 A1 | 8/2003 | Tsuji et al. |
| 2003/0170258 A1 | 9/2003 | Roy-Chowdhury et al. |
| 2004/0022768 A1 | 2/2004 | Roy-Chowdhury et al. |
| 2004/0023909 A1 | 2/2004 | Roy-Chowdhury et al. |
| 2004/0087485 A1 | 5/2004 | Ilan et al. |
| 2004/0171522 A1 | 9/2004 | Ilan et al. |
| 2004/0171526 A1 | 9/2004 | Ilan et al. |
| 2004/0171527 A1 | 9/2004 | Ilan et al. |
| 2004/0171528 A1 | 9/2004 | Flan et al. |
| 2004/0171557 A1 | 9/2004 | Ilan et al. |
| 2005/0069546 A1 | 3/2005 | Ilan et al. |
| 2006/0116331 A1 | 6/2006 | Jiang et al. |
| 2007/0010483 A1 | 1/2007 | Ilan et al. |
| 2007/0117778 A1 | 5/2007 | Ilan |
| 2009/0221516 A1 | 9/2009 | Tashiro et al. |

FOREIGN PATENT DOCUMENTS

| | | |
|---|---|---|
| EP | 0 957 161 A1 | 11/1999 |
| EP | 0957161 | 11/1999 |
| EP | 0 988 860 A1 | 3/2000 |
| EP | 0986860 | 3/2000 |
| EP | 1 072 271 A2 | 1/2001 |
| WO | WO 99/33475 | 7/1999 |
| WO | WO1999/033475 | 7/1999 |
| WO | WO2001/079152 | 10/2001 |
| WO | WO/02/051986 | 7/2002 |
| WO | WO2003/009812 | 2/2003 |
| WO | WO2003/027058 | 4/2003 |
| WO | WO 03/093287 A1 | 11/2003 |
| WO | WO2003/093287 | 11/2003 |
| WO | WO2005/032462 | 4/2005 |
| WO | WO2007/099999 | 9/2007 |

OTHER PUBLICATIONS

Adar and Ilan, "beta-Glycosphingolipids as immune modulators," *J Immunotoxicol.*, vol. 5, No. 2, pp. 209-220 (2008).
Feffer et al., "Thrombotic tendencies and correlation with clinical status in patients infected with HIV," *South Med. J.*, vol. 88, No. 11, pp. 1126-1130 (abstract only) (1995).
Gomez-Reino et al., "Inflammation and HIV infection: a friendly connection," *Lancet*, vol. 348, Suppl. II, p. 24 (1996).
Long et al., "Characterization of human immunodeficiency virus type 1 gp120 binding to liposomes containing galactosylceramide," *J. Virol.*, vol. 68, No. 9, pp. 5890-5898 (1994).
Buczko et al., "Aspirin and the fibrinolytic response," *Thrombosis Research*, vol. 110, pp. 331-334 (2003).
Di Micco et al., "Anti-thrombin action of low-dose acetylsalicylic acid," *European Journal of Pharmacology*, vol. 460, pp. 59-62 (2003).
Ramalho, Fernando, "Hepatitis C virus infection and liver steatosis," *Antiviral Research*, vol. 60, pp. 125-127 (2003).
Szczeklik et al., "Aspirin and thrombinogenesis" *Thrombosis Research*, vol. 110, pp. 345-347 (2003).
Zeller et al., "Influence of Valproate Monotherapy on Platelet Activation and Hematologic Values," *Epilepsia*, vol. 40, No. 2, pp. 186-189 (2009).
"Non-alcoholic fatty liver disease," Wikipedia, Aug. 9, 2016.
Ishihara et al., "α-Glycosylceramides Enhance the Antitumor Cytotoxicity of Hepatic Lymphocytes Obtained from Cancer Patients by Activating CD3⁻CD56⁺NK Cells In Vitro," *The Hournal of Immunology*. vol. 165, pp. 1659-1664 (2000).

(Continued)

*Primary Examiner* — Michelle S Horning
(74) *Attorney, Agent, or Firm* — Paul Diamond, Esq.

(57) ABSTRACT

The present invention provides a method for the treatment of immune mediated or immune related diseases or disorders, infectious diseases, metabolic disorders and cancer in mammalian subjects. This method comprises the administration of a naturally occurring, mammalian intermediary metabolite or T cell receptor ligand, preferably a glucosylceramide, to a mammalian subject. In a preferred embodiment, such mammalian subjects are human beings.

16 Claims, 19 Drawing Sheets

(56) References Cited

OTHER PUBLICATIONS

Motoki et al., "Antitumor Activities of α-, β-Monogalactysylceramides and Four Diastereomers of an α-Galactosylceramide," *Bioorganic & Medicinal Chemistry Letters*, vol. 5, No. 7. pp. 705-710 (1995).

Baldwin et al., "Do NSAIDs contribute to acute fatty liver of pregnancy?," *Medical Hypotheses*, vol. 54, No. 5, pp. 846-849 (2000).

Kaneda et al., "Inflammatory Liver Steatosis Caused by IL-12 and IL-18," *Journal of Interferon & Cytokine Research*, vol. 23, pp. 155-162 (2003).

Saygan-Karamürsel et al., "Acute fatty liver of pregnancy after aspirin intake," *J. Matern. Fetal Neonatal Med.*, vol. 16, No. 1, pp. 65-66 (2004).

Adar et al., "Increased red blood cell aggregation in patients with Gaucher disease is non-inflammatory," *Clinical Hemorheology and Microcirculation*, vol. 40, p. 113-118 (2008).

Adar et al., "beta-Glycosphingolipids as Immune Modulators," *Journal of Immunotoxicology*, vol. 5, pp. 209-220 (2008).

Adar et al., "Aggregation of red blood cells in patients with Gaucher disease," *British Journal of Haematology*, vol. 134, pp. 432-437 (2006).

Ajuebor et al., "Role of chemokines arid chemokine receptors in the gastrointestinal tract," *Immunology*, vol. 105, pp. 137-143 (2002).

Araki et al., "Synthetic Glycolipid Ligands for Human iNKT Cells as Potential Therapeutic Agents for Immunotherapy," *Current Medicinal Chemistry*, vol. 15, pp. 2337-2345 (2008).

Axford, "Glycobiology & Medicine: A Millenial Review," *GlycoScience*, Mar. 30, 2001.

Bendelac et al., "The Biology of NKT Cells," *Annu. Rev. Immunol.*, vol. 25, pp. 297-336 (2007).

Berzofsky et al., "Progress on new vaccine strategies against chronic viral infections," *J. Clin. Invest*, vol. 114, No. 4, pp. 450-462 (2004).

Bezbradica et al., "Distinct Roles of Dendritic Cells and B Cells in Va14Ja18 Natural T Cell Activation In Vivo," *The Journal of Immunology*, vol. 174 pp. 4696-4705 (2005).

Biburger et al., "Alpha-Galactosylceramide-Induced Liver Injury in Mice is Mediated by TNF-alpha but Independent of Kupffner Cells," *The Journal of Immunology*, vol. 175, pp. 1540-1550 (2005).

Brigl et al., "CD1: Antigen Presentation and T Cell Function," *Annu. Rev. Immunol.*, vol. 22, No. 817-890 (2004).

Brunt et al., "Nonalcoholic steatohepatitis: a proposal for grading and staging the histological lesions," *Am. J. Gastroenterol.*, vol. 94, No. 9, pp. 2467-2474 (1999).

Brutkiewicz et al., "CD1d-Mediated Antigen Presentation to Natural Killer T (NKT) Cells,"*Critical Review of Immunology*, vol. 23, Nos. 5 & 6, pp. 403-419 (2003).

Brutkiewicz et al., "CD1d Ligands: The Good, the Bad, and the Ugly," *The Journal of Immunology*, vol. 177, pp. 769-775 (2006).

Chiu et al., "Multiple defects in antigen presentation and T cell development by mice expressing cytoplasmic tail-truncated CD1d," *Nature immunology*, vol. 3, No. 1, pp. 55-60 (2002).

Cohen, *Science*, vol. 285 (5424), pp. 2630 (2001).

Creput et al., Cutaneous thrombotic microangiopathy during treatment with alpha-interferon for chronic hepatitis C, *J. Hepatol*, vol. 37, No. 6, pp. 871-872 (2002),871-2.

Curat et al., From Blood Monocytes to Adipose Tissue-Resident Macrophages Induction of Diapedesis by Human Mature Adipocytes, *Diabetes*, vol. 53, pp. 1285-1292 (2004).

Dao et al., "Development of CD1d-restricted NKT cells in the mouse thymus," *Dur. J. Immunol.*, vol. 34, pp. 3542-3552 (2004).

Darnell et al., "Jak-STAT Pathways and Transcriptional Activation in Response to IFNs and Other Extracellular Signaling Proteins," *Science New Series*, vol. 264, No. 5164, pp. 1415-1421 (1994).

Definition of "prevention" from the Institute for International Medical Education [online], [Retrieved on Mar. 24, 2011]. Retrieved from the Internet: http://www.iime.org/glossary.htm, Published Feb. 2002, p. 1, 2, 26, 27 and 39.

Degenerative nervous system diseases http://neurology.healthcares.net/degenerative-system.php> Jun. 26, 2005.

Degroote et al., "The cell biology of glycosphingolipids," *Semin Cell Dev Bilo*, vol. 15, No. 4, pp. 375-387 (2004).

Duwaerts et al., *Expert Opinion on Therapeutic Targets*, vol. 15, No. 8, pp. 973-988 (2011).

Elgert et al., "tumor Induced immune dysfunction: the macrophage connection," *Journal of Leukocyte Biology*, vol. 64, pp. 275-290 (1998).

Epstein et al., "The SCID-hu Myeloma Model," *Methods in Molecular Medicine*, vol. 113, pp. 183-190 (2005).

Exiley et al., "To Be or Not to Be NKT: Natural Killer T Cells in the Liver," *Hepatology*, vol. 40, pp. 1033-1040 (2004).

Fernandez-Real et al. "Insulin Resistance and Chronic Cardiovascular Inflammatory Syndrome," *Endocrine Reviews*, vol. 24, No. 3 pp. 278-301 (2003).

Gatenby, et al., "The Glycoiytic Phenotype in Carcinogenesis and Tumor Invasion: Insights through Mathematical Models," *Cancer Research*, vol. 63, pp. 3847-3854 (2003).

Ghosh et al., "Targeting of liposomes towards different cell types of rat liver through the involvement of lisposomal surface glycosides," *Arch Biochem Biophys*, vol. 213, No. 1, pp. 266-270 (1982).

Godfrey et al., "Going both ways: immune regulation via CD1d-dependent NKT cells," *J. Clinical Invest.*, vol. 114, pp. 1379-1388 (2004).

Godfrey et al., "The Elusive NKT Cell Antigen—is the Search Over?," *Science*, vol. 306, pp. 1687-1689 (2004).

Goker-Alpan et al., "Risky business: Gaucher disease and multiple myeloma," *Blood*, vol. 105 pp. 4546-4547 (2005).

Gokhan-Hotamisligil, "Inflammation and metabolic disorders," *Nature*, vol. 444, pp. 860-867 (2006).

Halder et al., "Type II NKT cell-mediated energy induction in type I NKT cells prevents inflammatory liver disease," *J. Clin. Invest.*, vol. 117, No. 8, pp. 2302-2312 (2007).

Hammond et al., "NKT cells: Potential targets for autoimmune disease therapy?," *Tissue Antigens*, vol. 59, pp. 353-363 (2002).

Hammond et al.., "Natural killer T cells: natural or unnatural regulators of autoimmunity?," *Current Opinion in Immunology*, vol. 15, pp. 683-689 (2003).

Hansen et al., "Regulation of immunity and pathogenesis in infectious diseases by CD1d-restricted NKT cells" *International Journal for Parasitology*, vol. 34, pp. 15-25 (2004).

Hansen, B.C., "The Metabolic Syndrome X," *Annals New York Academy of Sciences*, vol. 892, pp. 1-24 (1999).

Hansen-Flaschen, "Update in Pulmonary Medicine" *Ann. Intern. Med.*, vol. 138, pp. 319-325 (2003).

Haratz et al., "Autoimmune hemolytic anemia in Gaucher's disease," *Journal of Molecular Medicine*, vol. 68, No. 2, pp. 94-95 (1990).

Hoffman E.P., "Genetic Changes in Cancer: Second of three Parts" [online], [Retrieved on Apr. 14, 2011]. Retrieved from the internet: http://www.candlelighters.org/research/genetics2.aspx.

Holland, et al., "Inhibition of Ceramide Synthesis Ameliorates Glucocorticoid-, Saturated-Fat-, and Obesity-Induced Insulin resistance," *Cell Metabolism*, vol. 5, pp. 167-179 (2007).

Hotamisligil et al., "Adipose Expression of tumor Necrosis Factor-a: Direct Role in Obesity-Linked Insulin Resistance," *Science*, vol. 259, No. 5091, pp. 87-91 (1993).

Huang et al., "Recent development of therapeutics for chronic HCV infection," *antiviral Res.*, vol. 71, pp. 351-362 (2006).

Huber et al., Role of CD1d in Coxsackievirus B3-Induced Myocarditis, *The Journal of Immunology*, vol. 170, pp. 3147-3153 (2003).

Ilan et al., "Alleviation of Acute and Chronic Graft-Versus-Host Disease in a Murine Model is Associated with Glucocerebroside-Enhanced Natural Killer T Lymphocyte Plasticity," *Transplantation*, vol. 83, No. 4, pp. 458-467 (2007).

"Immune System" from Kids-Health [online]. [Retrieved Mar. 24, 2011]. Retrieved from the internet: http://kidshealth.org/teen/your_body/body_basics/immune.html, Published Jun. 18, 2007.

(56) References Cited

OTHER PUBLICATIONS

"Immunodeficiency Disorders" from the Merck Manual Home Edition [online]. [Retrieved Mar. 18, 2011]. Retrieved from the internet: http://www.merckmanuals.com/home/print/sec16/ch184/ch184a.html.

Jaruga et al., "Crucial Role of IL-4/STAT6 in T Cell-Mediated Hepatitis: Up-Regulating Eotaxins and IL-5 and Recruiting Leukocytes," *The Journal of Immunology*, vol. 171, pp. 3233-3244 (2003).

Kaneko et al., "Augmentation of Valpha14 NKT Cell-mediated Cytotoxicity by Interleukin 4 in an Autocrine Mechanism Resulting in the Development of Concanavalin A-induced Hepatitis" *J. Exp. Med.*, vol. 191, No. 1, pp. 105-114 (2000).

Keneto et al., "Oxidative Stress and the JNK Pathway in Diabetes," *Current Diabetes Review*, vol. 1, pp. 65-72 (2005).

Kershaw et al., "Adipose Tissue as an Endocrine Organ," *J Clin Endocrinol Metab*, vol. 89, 2548-2556 (2004).

Khan et al., *Journal of Virology*, vol. 88, No. 21, pp. 12276-12295 (2014).

Kobayashi et al., "Enhancing effects of alpha-, beta-monoglycosylceramides on natural killer cell activity," *bioorganic & Medicinal Chem.*, vol. 4, No. 4, pp. 615-610 (1996).

Kodama et al., "c-Jun N-Terminal Kinase Sionaling in the Pathogenesis of Nonalcoholic Fatty Liver Disease: Multiple Roles in Multiple Steps," *Hepatology*, vol. 49, pp. 6-8 (2009).

Koziel et al., "Hepatitis C virus (HCV)-specific cytotoxic T lymphocytes recognize epitopes in the core and envelope proteins of HCV," *J. Virol*, Vo. 67, No. 12, pp. 7522-7532 (1993).

Kronenberg et al., Toward an Understanding of NKT Cell Biology: Progress and Paradoxes, *Annu. Rev. Immunol.* vol. 26, pp. 877-900 (2005).

Lalazar et al., "Glycolipids as Immune Modulatory Tools," *Mini-Reviews in Medicinal Chemistry*, vol. 6, pp. 1249-1253 (2006).

Lalazar et al., "beta,Giycosphingolipids-mediated lipid raft alteration is associated with redistribution of NKT cells and increased intrahepatic COB+ T lymphocyte trapping," *J. Lipid Res*, vol. 49, pp. 1884-1893 (2008).

Lalazar et al., "Modulation of intracellular machinery by beta-glycolipids is associated with alteration of NKT lipid rafts and amelioration of concanavalin-induced hepatitis," *Molecular Immunology*, vol. 45, pp. 3517-3525 (2008).

Landgren et al., "Risk of malignant disease among 1525 adult male US veterans with Gaucher disease," *Arch Intern Med*, vol. 167, pp. 1189-1194 (2007).

Liang, *Nature Medicine*, vol. 19, No. 7, pp. 869-878 (2013).

Lippincott, "The Hepatitis C Viruses," *Fields Virology*, vol. 1, pp. 1004-1016 (2001).

Liu et al., JNK: Bridging the insulin signaling and inflammatory pathway, *Current Opinion in Investigational Drugs*, vol. 6, No. 10, pp. 979-987 (2005).

Livovsky et al., Administration of beta-glycolipids overcomes an unfavorable nutritional dependent host milieu: a role 42 for a soy-free diet and natural ligands in intrahepatic COB+ lymphocyte trapping and NKT cell redistribution, *International Immunopharmacology*, vol. 8, pp. 1298-1305 (2008).

Luc Van Kaer, α-Galactosylceramide therapy for autoimmune disease: prospects and obstacles, *Nature Revs*, Immunology, vol. 18, No. 7, pp. 31-42 (1997).

Luc Van Kaer, "NKT cells: T lymphocytes with innate effector functions," *Curr. Opin. In Immunology*, vol. 19, pp. 354-364 (2007).

Mackay, et al., "Autoimmune Diseases," *New England Journal of Medicine*, vol. 345, No. 5, pp. 340-350 ((2001).

Major et al., "Hepatitis C Viruses," *Fields Virology*, vol. 1, pp. 1127-1161 (2001).

Makowska et al., "Differences in the Ligand Specificity between CD1d-Restricted T Cells with Limited and Diverse T-Cell Receptor Repertoire," *Scand. J. Immunol.*, vol. 52, pp. 71-79 (2000).

Malhi et al., "Molecular Mechanisms of Lipotoxicity in Nonalcoholic Fatty Liver Disease," *Semin Liver Dis*, vol. 28, pp. 360-369 (2008).

Marra et al., "Expression of the thrombin receptor in human liver: up-regulation during acute and chronic injury," *Hepatology*, vol. 27, No. 2, pp. 462-471 (1998).

Matteoni et al., "Nonalcoholic Fatty Liver Disease: A Spectrum of Clinical and Pathological Severity," *Gastroenterology*, vol. 116, pp. 1413-1419 (1999).

Mayeux et al., "Epidemiology of Neurodegeneration," *Annu. Rev. Neurosci.*, vol. 26, pp. 81-104 (2003).

Merck Manual Home Edition, subject "Viral Infections" [online], [Retrieved on Oct. 16, 2008]. Retrieved from the internet: http://www.merck.com/mmhe/print/sec17/ch198/ch198a.html.

Mitsui et al., "Mutations for Gaucher Disease Confer High Susceptibility to Parkinson Disease," *Arch Neural.*, vol. 66, No. 5, pp. 571-576 (2009).

Miyagi et al., Concanavalin A Injection Activates Intrahepatic Innate Immune Cells to Provoke an Antitumor Effect in Murine Liver, *Hepatology*, vol. 40, pp. 1190-1196 (2004).

Miyake et al., "Therapeutic Potential of Glycolipid Ligands for Natural Killer (NK) T Cells in the Suppression of Autoimmune Diseases," *Current Drug Targets-Immune, Endocrine & Metabolic Disorders*, vol. 5, pp. 5315-5322 (2005).

Miyake et al., NKT Cells and Autoimmune Diseases. Unraveling the Complexity, *Curr. Top. Microbiol. Immunol.*, vol. 314, pp. 251-265 (2007).

Mizrahi et al., "beta-Giycoglycosphingolipid-induced augmentation of the anti-HBV immune response is associated with altered COB and NKT lymphocyte distribution: A novel adjuvant for HBV vaccination," *Vaccine*, vol. 26, pp. 2589-2595 (2008).

Motoki et al., "Immunostimulatory and antitumor activities of monoglycosylceramides having various sugar moieties," *boil. Phar. Bull.*, vol. 18, No. 11, pp. 1487-1491 (1995).

Nandi et al., "Biologically active, recombinant DNA in clathyrin-coated vesicles isolated from rat livers after in vivo injection of liposome-encapsulated DNA," *J Biol Chem.*, vol. 261, No. 35, pp. 16722-16726 (1986).

"Neurological disorders" from health-cares.net [online], [retrieved Jan. 6, 2010]. Retrieved from the internet: http://neurology.health-cares.net/>, published online Feb. 7, 2005.

Nicolau et al., "Liposomes as carriers for in vivo gene transfer and expression," *Methods Enzymol.*, vol. 149, pp. 157-176 (1987).

Nicoletti et al., "Murine Concanavalin A-induced hepatitis is prevented by interleukin 12 (IL-12) antibody and exacerbated by exogenous IL-12 through an interferon-gamma-dependent mechanism," *Hepatology*, vol. 32, pp. 728-733 (2000).

Oh et al., "Role of type II NKT cells in the suppression of graft-versus-host disease," *Crit. Rev. Immunol.*, vol. 28, No. 3, pp. 249-267 (2008).

Oki et al., The clinical implication and molecular mechanism of preferentiaiiL-4 production by modified glycolipid- stimulated NKT cells, *J. Clin. Invest.*, vol. 113, pp. 1631-1640 (2004).

Onoe et al., "Th1 or Th2 balance regulated by interaction between dendritic cells and NKT cells," *Immunol Res*, vol. 38, pp. 319-332 (2007).

Ortaldo et al, "Dissociation of NKT Stimulation, Cytokine Induction, and NK Activation In Vivo by the Use of Distinct TCR-Binding Ceramides," *J Immunol*, vol. 172, pp. 943-953 (2004).

Osman et al., "Activation of hepatic NKT cells and subsequent liver injury following administration of alpha-galactosylceramide," *Eur. J. Immunol.*, vol. 30 pp. 1919-1928 (2000).

Porubsky et al., "Normal development and function of invariant natural killer T cells in mice with Isoglobotrihexosylceramide (iGb3) deficiency," *PNAS*, vol. 104, No. 14, pp. 5977-5982 (2007).

Racanelli et al., "Presentation of HCV antigens to naïve CD8+T cells: why the where, when, what and how are important for virus control and infection outcome," *Clin Immuno,*, vol. 124, No. 1, pp. 5-12 (2007).

Rollier et al., "Control of Heterologous Hepatitis C Virus Infection in Chimpanzees is Associated with the Quality of Vaccine-Induced Peripheral T-Helper Immune Response," *J. Virol*, vol. 78, No. 1, pp. 187-196 (2004).

Rouhl, A.M., "Metabolic Syndrome," *Chemical & Engineering News*, vol. 82, No. 47, pp. 83-99 (2004).

(56) References Cited

OTHER PUBLICATIONS

Sandberg et al., "Development and function of CD1d-restricted NKT cells: influence of sphingolipids, SAP and sex," *Trends in Immunology*, vol. 26 pp. 347-349 (2005).
Selkoe et al., "Alzheimer's disease: Genes, proteins, and therapy," *Physiol. Rev.*, vol. 81, No. 2, pp. 741-766 (2001).
Shevach Ethan, "From vanilla to 28 flavors: Multiple varieties of T regulatory cells," *Immunity*, vol. 25, pp. 195-201 (2006).
Singh et al., "Natural Killer T Cell Activation Protects Mice Against Experimental Autoimmune Encephalomyelitis," *J. Exp. Med.*, vol. 194, No. 12, pp. 1801-1811 (2001).
Singh et al. "Differential Effects of JNK1 and JNK2 Inhibition or Murine Steatohepatits and Insulin Resistance," *Hepatology*, vol. 49, pp. 87-96 (2009).
Skold et al, "Role of CD1d-Restricted NKT Cells in Microbial Immunity," *Infection and Immunity*, vol. 71, No. 10, pp. 5447-5455 (2003).
Slife et al., "Free sphingosine formation from endogenous substrates by a liver plasma membrane system with a divalent cation dependence and a neutral pH optimum," *J Biol. Chem.*, vol. 254, No. 18, pp. 10371-10377 (1989).
Smith et al., "Traditional sampling with laboratory analysis and solid phase microextraction sampling with field gas chromatography/mass spectrometry by military industrial hygienists," *AIHA Journal*, vol. 63, pp. 284-292 (2002).
Stanic et al., "Another View of T Cell Antigen Recognition: Cooperative Engagement of Glycolipid Antigens by Va14Ja18 Natural TCR," *The Journal of Immunology*, vol. 171, pp. 171-184 (2003).
Stanic et al., Innate self recoanition by an invariant, rearranged T-cell receptor arid its immune consequences, *Immunology*, vol. 109, pp. 4639-4551 (2003).
Summers, et al., "A Role for Sphingolipids in Producing the Common Features of Type 2 Diabetes, Metabolic Syndrome X, and Cushing's Syndrome," *Diabetes*, vol. 54, pp. 591-602 (2005).
Stevenson et al., "The epidemiology of influenza," *Occup. Med.*, vol. 52, (2002)—Abstract Only.
Sweeley, "Glycosphingolipids: structure and function," *Pure & Appl. Chem.*, vol. 61, No. 7, pp. 1307-1312 (1989).
Takeda et al., *Human Cell*, vol. 14. No. 3, pp. 159-163 (2001).
Takeda et al., "Critical contribution of liver natural killer T cells to a murine model of hepatisis," *PNAS*, vol. 97, No. 10, pp. 5498-5503 (2000).
Tan et al., "Strategies for hepatitis C therapeutic intervention: now and next," *Curr. Opin in Pharmacology*, vol. 4, pp. 465-470 (2004).
Taniguchi et al., "The regulatory role of Valpha14 NKT cells in innate and acquired immune response," *Annu. Rev. Immunol.*, vol. 21, pp. 483-513 (2003).
Tessmer et al., "NKT cell immune responses to viral infection," *Expert Opin. Ther. Targets*, vol. 13. No. 2, pp. 153-162 (2009).
Tiegs et al., "Cellular and Cytokine-Mediated Mechanisms of Inflammation and its Modulation in Immune-Mediated Liver Injury," *Gastroenterol*, vol. 45, pp. 63-70 (2007).
Todar, K., "Bacterial Resistance to Antibotics," in Todar's Online Textbook of Bacteriology [online], [Retrieved on Dec. 28, 2008]. Retrieved from the internet: http://www.textbookofbacteriology.net/resantimicrobial.html, pp. 1-4.
Tomura et al., "A Novel Function of Valpha14+CD4+NKT Cells: Stimulation of IL-12 Production by Antigen-Presenting Cells in the Innate Immune System," *J Immunol*, vol. 163, pp. 93-101 (1999).
Torisu et al., "Suppressor of Cytokine Signaling 1 Protects Mice Against Concanavalin A-Induced Hepatitis by Inhibiting Apoptosis, *Hepatology*, vol. 47. pp. 1644-1654 (2008).
Trayhurn et al., "Adipose Tissue and Adipokines-Energy Regulation from the Human Perspective," *J. Nutr.*, vol. 136, pp. 1935S-1939S (2006).
Trinchera et al., "Recycling of glucosylceramide and sphingosine for the biosynthesis of gangliosides and sphingomyelin in rat liver," *Biochem J.*, vol. 270, No. 3, pp. 815-820 (1990).
Tsuji et al., "Glycolipids and phospholipids as natural CD1d-binding NKT cell ligands," *Cell. Mol. Life Sci.*, vol. 63, pp. 1889-1898 (2006).
Tupin at al., "The unique role of natural killer T cells in the response to microorganisms," *Nature Rev. Microbiology*, vol. 5, pp. 405-417 (2007).
Uemura et al., "Role of human non-invariant NKT lymphocytes in the maintenance of type 2 T helper environment during pregnancy," *International Immunology*, vol. 20, No. 3, pp. 405-412 (2008).
Van der Vliet et al., Immunology, vol. 98, pp. 557-563 (1999).
Vanderkerken et al., "The 5T2MM murine model of multiple myeloma," *Methods in Mol. Med.*, vol. 113, pp. 191-205 (2005).
Weisberg et al. "Obesity is associated with macrophage accumulation in adipose tissue," *J. Clin. Invest.*, vol. 112, pp. 1796-1808 (2003).
Wilson et al., "Natural Killer T Cells as Targets for Therapeutic Intervention in Autoimmune Diseases," *Current Pharmaceutical Design*, vol. 9, pp. 201-220 (2003).
Xu et al., "Chronic inflammation in fat plays a crucial role in the development of obesity-related insulin resistance," *J. Clin. Invest.*, vol. 112, pp. 1821-1830 (2003).
Yamamura et al., "NKT Cell-Stimulating Synthetic Glycolipids as Potential Therapeutics for Autoimmune Disease," *Current Topics in Medicinal Chemistry*, vol. 4, pp. 561-657 (2004).
Yang et al., "Role of Interferon-y in GVHD and GVL," *Cellular & Molecular Immunology*, vol. 2, No. 5, pp. 323-329 (2005).
Yu et al., "Production and characterization of monoclonal antibodies against complexes of the NKT cell ligand a- galactosylceramide bound to mouse CD1d," *Journal of Immunological Methods*, vol. 32, pp. 11-23 (2007).
Yu et al., "Modulation of CD1d-restricted NKT cell responses by using N-acyl variants of alpha-galactosyiceramides," *PNAS*, vol. 102, No. 9, pp. 3383-3388 (2005).
Zajonc et al., "Structure and function of a potent agonist for the semi-invariant natural killer T cell receptor," Nature Immunology, vol. 6, No. 8., pp. 810-818 (2005).
Zhou et al., "The Immunological Function of iGb3," *Current Protein and Peptide Science*, vol. 7, pp. 325-333 (2006).
Zigmund et al., "Treatment of non-alcoholic steatohepatitis by beta-glucoceramide: A phase 1/11 clinical study," *Hepatology*, vol. 44, pp. 180A (2006).
Zigmund et al., "beta-Glucosylceramide: a novel method for enhancement of natural killer T lymphoycte plasticity in murine models of immune-mediated disorders," *Gut*, vol. 56, pp. 82-89 (2007).
Zigmund et al., "beta-Giycosphingolipids improve glucose intolerance and hepatic steatosis of the Cohen diabetic rat," *Am J Physiol Endocrinol Metab*, vol. 296, pp. E72-E78 (2009).
Zitzmann et al., "Abnormal Glycosylation in Disease and Therapy: Relevance to Chronic Viral Infections," The Glycobiology Institute, Dept. of Biochemistry, Oxfor University, Oxford, United Kingdom; Viral Hepatitis Group, Kimmel Cancer Center, Jefferson Medical College, Philadelphia, Pennsylvania, USA, 1999 (Abstract only).
Maragoudakis et al., "Effects of thrombin/thrombosis in angiogenesis and tumour progression," *Matrix Biology*, vol. 19, pp. 345-351 (2000).
U.S. Appl. No. 11/378,941, filed Mar. 17, 2006.
U.S. Appl. No. 10/451,811, filed Jun. 25, 2003, Ilan et al.
U.S. Appl. No. 10/375,906, filed Feb. 27, 2003, Ilan et al.
U.S. Appl. No. 08/808,629, filed Feb. 28, 1997, Roy-Chowdhury et al.
U.S. Appl. No. 10/377,628, filed Mar. 4, 2003, Roy-Chowdhury et al.
U.S. Appl. No. 10/377,603, filed Mar. 4, 2003, Roy-Chowdhury et al.
U.S. Appl. No. 09/447,704, filed Feb. 28, 1997, Roy-Chowdhury et al.
U.S. Appl. No. 09/356,294, filed Jul. 16, 1999, Roy-Chowdhury et al.
U.S. Appl. No. 10/385,440, filed May 9, 2001, Roy-Chowdhury et al.
Dwek, RA., Block, TM, Nichita-Branza, N., Petrescu, S., Platt, F., Rudd, PM, Zitzmann, N., "Abnormal glycosylation in disease and

(56) References Cited

OTHER PUBLICATIONS therapy", Proceedings of the Royal Society of Medicine's 5th Jenner Symposium (Glycobiology and Medicine conference), Jul. 10-11, 2000.
Axford. Glycobiology & Medicine: A millennial Review, Jul. 2000.
Beecher, WC, Metabolic profiling: Its role in biomarker discovery and gene function analysis, Chapter 17: The human metabolome. Kluwer Academic, 2003.
Margalit et al. Glucocerebroside treatment ameliorates ConA hepatitis by inhibition of NKT lymphocytes. Am. J. Physiol. Gastrointest. Liver Physiol., Nov. 2005, Abstract.
Margalit et al. Amelioration of hepatic fibrosis via beta-glucoceramide mediated immune modulation is associated with NKT lymphocyte distribution and a cytokine shift. Am. Assoc. for Study of Liver Diseases, Meeting, Nov. 2005.
Margalit et al. Suppression of hepatocellular carcinoma by glucocerebroside is associated with altered NKT and CD8+ lymphocyte distributions, stat1 expression, lack of stat6 expression and a Th1 type immune response. Am Assoc. for Disease of Liver, Oct. 200, Abstract.
Zigmond et al., Facilitation of hapatocellular carcinaoma growth in mice by double negative NKT regulatory lymphocytes is inhibited by ex vivo exposure to beta-glucosylceramide. Am Assoc. for Study of Liver Diseases, Meeting, Nov. 2005.
Knipe, DM, Howley, PM, eds. Fields virology. 4th ed. vol. 1. Philadelphia: Lippincott Williams & Wilkins, 2001, 1004-1016 and 1127-1161.
Hahn. Subversion of immune responses by hepatitis C virus: immunomodulatory strategies beyond evasion? Current opinion in immunology, 2003, vol. 15, 443-449.
De Francesco et al., Challenges and successes in developing new therapies of hepatitis C. Nature, 2005, vol. 436, 953-960.
Schoenfeld, Y., et al, "Gaucher's disease: a disease with chronic stimulation of the immune system," Arch Pathol Lab Med 106(8):388-391 (1982).
Lichtenstein, et al, "Cytokine mRNA in Gaucher Disease," Blood Cells, Molecules and Diseases 23(19):395-401 (1997).
Barak, V., et al, "Cytokines in Gaucher's Disease," Eur. Cytokine Netw. 10(2):205-210 (1999).
Hollak, CEM, et al, "Elevated Levels of M-CSF, sCD14 and IL8 in Type 1 Gaucher Disease," Blood Cells, Molecules and Diseases 23(11):201-212 (1997).
Allen, MJ, et al, "Pro-inflammatory cytokines and the pathogenesis of Gaucher's disease: increased release of interleukin-6 and interleukin-10," Q. J. Med. 90(1):19-25 (1997).
Deibener, J., et al, "Enzyme replacement therapy decreases hypergammaglobulinemia in Gaucher's disease," Haematologica 83:479-480 (1998).
Lachman, et al., "Massive hepatic fibrosis in Gaucher's disease: clinico-pathological and radiological features," Q. J. Med 93:237-244 (2000).
Kawano, et al, "CD1d-Restricted and TCR-Mediated Activation of $V_\alpha 14$ NKT Cells by Glycosylceramides," Science 278:1626-1629 (1997).
Burdin, N., et al, "Selective Ability of Mouse CD1 to Present Glycolipids: $_\alpha$-Galactosylceramide Specifically Stimulates $V_\alpha 14^+$NK T Lymphocytes," J. Immunol 161:3271-3281 (1998).
Hollak, et al, "Marked elevation of plasma chitotriosidase activity. A novel hallmark of Gaucher disease," J. Clin. Invest. 93(3):1288-1292 (1994).
Ferrari, C., et al, "Immunopathogenesis of hepatitis C virus infection," J. Hepatol 31s1:31-38 (1999).
Cerny, A., et al, "Pathogenesis of chronic hepatitis C: immunological features of hepatic injury and viral persistence," Hepatology 30(3):595-601 (1999).
Rehermann, B., "Cellular immune response to the hepatitis C virus," J. Viral Hepat. 6s1:31-35 (1999).
Gotsman, I., et al, "Induction of oral tolerance towards hepatitis B envelope antigens in a murine model," Antiviral Research 48:17-26 (2000).

Akbar, SM, et al, "Low responsiveness of hepatitis B virus-transgenic mice in antibody response to T-cell-dependent antigen: defect in antigen presenting activity of dendritic cells", Immunology 78(3):468-475 (1993).
The complete listing of diseases is retrieved from http://www.mic.ki.se/Diseases/Alphalist.html.
Takahashi, M., Nakamura, K., Honda, K., Kitamura, Y., Mitzutani, T., Araki, Y., Kabemura, T., Chijiiwa, Y., Harada, N., Nawata, H., "An inverse correlation of human peripheral blood regulatory T cell frequency with the disease activity of ulcerative colitis", Dig Dis Sci. Apr. 2006 51(4): 677-86, (Abstract only).
Bode, JG., Ludwig, S., Ehrhardt, C., Albrecht, U., Erhardt, A., Schaper, F., Heinrich, PC, Haussinger, D., "IFN-alpha antagonistic activity of HCV core protein involves induction of suppressor of cytokine signaling-3", FASEB J. Mar. 2003; 17(3):488-90 Epub Jan. 22, 2003.
Margalit, M., et al., "Glucocerebroside Treatment Ameliorates Con-A Hepatitis by Inhibition of NKT Lymphocytes: A New Immunemodulatory Tool," Hepatology 38:163A (2003).
Bleicher, P.A., et al., "Expression of murine CD1 on gastrointestinal epithelium," Science 250:679-682 (1990).
Collins, C., et al., "RAG1, RAG2 and pre-T cell receptor alpha chain expression by adult human hepatic T cells: evidence for extrathymic T cell maturation," Eur. J. Immunol. 26:3114-3118 (1996).
Madsen, K.L., et al., "Interleukin 10 prevents cytokine-induced disruption of T84 barrier integrity and limits chloride secretion," Gastroenterology 113:151-159 (1997).
Mitchell, D.G., et al., "Fatty liver. Chemical shift phase-difference and suppression magnetic resonance imaging techniques in animals, phantoms, and humans," Invest. Radiol. 26:1041-1052 (1991).
Namimoto, T., et al., "Adrenal Masses: Quantification of Fat Content with Double-Echo Chemical Shift In-Phase and Opposed-Phase FLASH MR Images for Differentiation of Adrenal Adenomas," Radiology 218:642-646 (2001).
Sullards, M.C., et al., "Structure determination of soybean and wheat glucosylceramides by tandem mass spectrometry," J. Mass Spectrometry 35:347-353 (2000).
Trop, S., et al., "Liver-Associated Lymphocytes Expressing NK1.1 Are Essential for Oral Immune Tolerance Induction in a Murine Model," Hepatology 29:746-755 (1999).
Vicari, A.P., et al., "Mouse NK1.1+ T cells: a new family of T cells," Immunology Today 17(2):71 (1996).
Smyth et al. (2002) Current Opinion in Immunology. 14: 165-171.
Vliet et al. (1999) Immunology. 98:557-563.
Connolly and Cunningham (2000) European Journal of Anaesthesiology. 17: 219-220.
U.S. Appl. No. 09/447,704, filed Nov. 23, 1999, Row-Chowdhury et al.
"Immune System" from Kids-Health [online]. [Retrieved Mar. 24, 2011]. Retrieved from the internet: http://kidshealth.org/teen/your_body/body_basics/immune.html. Published Jun. 18, 2007.
"Neurological disorders" from health-cares.net [online], [retrieved Jan. 6, 2010]. Retrieved from the internet: http://neurology.health-cares.net/>, published online Feb. 7, 2005.
Ajuebor et al., "Role of chemokines and chemokine receptors in the gastrointestinal tract," Immunology, vol. 105, pp. 137-143 (2002).
Alba and Lindor, "Non-alcoholic fatty liver disease," Alimentary Pharmacology & Therapeutics, vol. 17, Issue 8, pp. 977-986 (2003).
Axford, Glycobiology & Medicine: A Milenial Review, Jul. 2000.
Belchetz et al., "Treatment of Gaucher's Disease with Liposome-Entrapped Glucocerebroside: beta-Glucosidase," Lancet, vol. 2, No. 8029, pp. 116-117 (1977).
Berzofsky et al., "Progress on new vaccine strategies against chronic viral infections," J. Clin Invest, vol. 114, No. 4, pp. 450-462 (2004).
Bezbradica et al., "Distinct Roles of Dendritic Cells and B Cells in Va14Ja18 Natural T Cell Activation In Vivo," The Journal of Immunology, vol. 174, pp. 4696-4705 (2005).
Brigl et al., "CD1: Antigen Presentation and T Cell Function," Annu. Rev. Immunol., vol. 22, pp. 817-890 (2004).

(56) References Cited

OTHER PUBLICATIONS

Brutkiewicz et al., "CD1d-Mediated Antigen Presentation to Natural Killer T (NKT) Cells," *Critical Review in Immunology*, vol. 23, Nos. 5 & 6, pp. 403-419 (2003).
Connolly et al., *European Journal of Anaesthesiology*, vol. 17, pp. 219-220 (2000).
Degenerative nervous system diseases http://neurology.healthcares.net/degenerative-systemphp> Jun. 26, 2005.
Feffer et al., "Thrombotic tendencies and correlation with clinical status in patients infected with HIV," *South Med. J.*, vol. 68, No. 11, pp. 1126-1130 (abstract only) (1995).
Fernandez-Real et al., "Insulin Resistance and Chronic Cardiovascular Inflammatory Syndrome," *Endocrine Reviews*, vol. 24, No. 3 pp. 278-301 (2003).
Gatenby, et al., "The Glycolytic Phenotype in Carcinogenesis and Tumor Invasion: Insights through Mathematical Models," *Cancer Research*, vol. 63, pp. 3847-3854 (2003).
Halder et al., "Type II NKT cell-mediated energy induction in type I NKT cells prevents inflammatory liver disease," *J. Clin. Invest*, vol. 117, No. 8, pp. 2302-2312 (2007).
Hansen et al., "Regulation of immunity and pathogenesis in infectious diseases by CD1d-restricted NKT cells," *International Journal for Parasitology*, vol. 34, pp. 15-25 (2004).
Hansen-Flaschen, "Update in Pulvonary Medicine," *Ann. Intern. Med.*, vol. 138, pp. 319-325 (2003).
Hoffman, E.P., "Genetic Changes in Cancer: Second of three Parts" [online], [Retrieved on Apr. 14, 2011]. Retrieved from the internet: http://www.candlelighters.org/research/genetics2.aspx.
Huber et al., 37 Role of CD1d in Coxsackievirus B3-Induced Myocarditis, *The Journal of Immunology*, vol. 170, pp. 3147-3153 (2003).
Ishihara et al., "α-Glycosylceramides Enhance the Antitumor Cytotoxicity of Hepatic Lymphocytes Obtained from Cancer Patients by Activating CD3-CD56$^+$NK Cells In Vitro," *The Hournal of Immunology*, vol. 165, pp. 1659-1664 (2000).
Kaneko et al., "Augmentation of Valpha14 NKT Cell-mediated Cytotoxicity by Interleukin 4 in an Autocrine Mechanism Resulting in the Development of Concanavalin A-induced Hepatitis," *J. Exp. Med.*, vol. 191, No. 1, pp. 105-114 (2000).
Kaneto et al., "Oxidative Stress and the JNK Pathway in Diabetes," *Current Diabetes Review*, vol. 1, pp. 65-72 (2005).
Kershaw et al., "Adipose Tissue as an Endocrine Organ," *J Clin Endocrinol Metab*, vol., 89, 2548-2556 (2004).
Kobayashi et al., "Enhancing effects of alpha-, beta-monoglycosylceramides on natural killer cell activity," *bioorganic & Medicinal Chem.*, vol. 4, No. 4, pp. 615-619 (1996).
Kodama et al., "c-Jun N-Terminal Kinase Signaling in the Pathogenesis of Nonalcoholic Fatty Liver Disease: Multiple Roles in Multiple Steps," *Hepatology*, vol. 49, pp. 6-8 (2009).
Lalazar et al., "beta-Giycosphingolipids-mediated lipid raft alteration is associated with redistribution of NKT cells and increased intrahepatic COB+ T lymphocyte trapping," *J. Lipid Res*, vol. 49, pp. 1884-1893 (2008).
Laporte et al., *Am J. Respir Crit Care Med.*, vol. 164, No. 1, pp. 141-148 (2001).
Lee et al., *J. Exp. Med.*, vol. 195, No. 5, pp. 637-641 (2002).
Lengle et al., "Arterial thrombosis in ulcerative colitis, Transcatheter thrombolytic therapy," *West J Med.*, vol. 162, No. 6, pp. 543-547 (1995).
Luc Van Kaer, a-Galactosylceramide therapy for autoimmune disease: prospects and obstacles, *Nature Revs. Immunology*, vol. 18, No. 7, pp. 31-42 (1997).
Margalit et al., "Glucocerebroside treatment ameliorates ConA hepatitis by inhibition of NKT lymphocytes," *Am. J. Physiol.*, vol. 289, No. 5, pp. G917-G925 (2005).
Margalit et al., "Glucocerebroside ameliorates the metabolic syndrome in OB/OB mice," *J. Pharmacol. Exp. Ther.*, vol. 319, No. 1, pp. 105-110 (2006).

Mara et al., "Expression of the thrombin receptor in human liver: up-regulation during acute and chronic injury." *Hepatology*, vol. 27, No. 2, pp. 462-471 (1998).
Matsuda et al., *J Exp. Med.*, vol. 192, No. 5, pp. 741-754 (2000).
Miyake et al., NKT Cells and Autoimmune Diseases: Unraveling the Complexity, *Curr. Top. Microbiol. Lmmunol.*, vol. 314, pp. 251-265 (2007).
Miyake et al., "Therapeutic Potential of Glycolipid Ligands for Natural Killer (NK) T Cells in the Suppression of Autoimmune Diseases," *Current Drug Targets-Immune, Endocrine & Metabolic Disorders*, vol. 5, pp. 315-322 (2005).
Mizrahi et al., "beta-Giycoglycosphingolipid-induced augmentation of the anti-HBV immune response is associated with altered COB and NKT lymphocyte distribution: A novel adjuvant for HBV vaccination," *Vaccine*, vol. 26, pp. 2569-2595 (2008).
Motoki et al., "Antitumor Activities of α-, β-Monogalactysylceramides and Four Diastereomers of an α-Galactosylceramide," Bioorganic & Medicinal Chemistry Letters, vol. 5, No. 7, pp. 705-170 (1995).
Motoki et al., "Immunostimulatory and antitumor activities of monoglycosylceramides having various sugar moieties," *boll. Phar. Bull.*, vol. 18, No. 11, pp. 1487-1491 (1995).
Oki et al., 37 The clinical implication and molecular mechanism of preferentiaiiL-4 production by modified glycolipid-stimulated NKT cells, *J. Clin. Invest.*, vol. 113, pp. 1631-1640 (2004).
Ortaldo et al., "Dissociation of NKT Stimulation, Cytokine Induction, and NK Activation In Vivo by the Use of Distinct TCR-Binding Ceramides," *J Immunol*, vol. 172, pp. 943-953 (2004).
Osman et al., "Activation of hepatic NKT cells and subsequent liver injury following administration of alpha- galactosylceramide," *Eur. J. Immunol.*, vol. 30, pp. 1919-1928 (2000).
Racanelli et al., "Presentation of HCV antigens to naïve CD8+T cells: why the where, when, what and how are important for virus control and infection outcome," *Clin Immunol,*, vol. 124, No. 1, pp. 5-12 (2007).
Sandberg et al., "Development and function of CD1d-restricted NKT cells: influence of sphingolipids, SAP and sex," *Trends in Immunology*, vol. 26, pp. 347-349 (2005).
Saygan-Karamursel et al., "Acute fatty liver of pregnancy after aspirin intake," *J. Matern. Fetal Neonatal Med.*, vol. 16, No. 1, pp. 65-66 (2004).
Singh et al., "Differential Effects of JNK1 and JNK2 Inhibition on Murine Steatohepatitis and Insulin Resistance," *Hepatology*, vol. 49, pp. 87-96 (2009).
Slife et al., "Free sphingosine formation from endogenous substrates by a liver plasma membrane system with a divalent cation dependence and a neutral pH optimum," *J Biol. Chem.*, vol. 264, No. 18, pp. 10371-10377 (1969).
Smyth et al.,, *Current Opinion in Immunology*, vol. 14, pp. 165-171 (2002).
Stanic et al., Innate self recognition by an invariant, rearranged T-cell receptor and its immune consequences, *Immunology*, vol. 109, pp. 4539-4551 (2003).
Sullards et al., *J. Mass Spectrom.*, vol. 35, No. 3, pp. 347-353 (2000).
Szczeklik et al., "Aspirin and thrombinogenesis," *Thrombosis Research*, vol. 110, pp. 345-347 (2003).
Takeda et al., "Critical contribution of liver natural killer T cells to a murine model of hepatitis," *PNAS*, vol. 97, No. 10, pp. 5498-5503 (2000).
Takeda et al., *Human Cell*, vol. 14, No. 3, pp. 159-163 (2001).
Tessmer et al., "NKT cell immune responses to viral infection," *Expert Opin. Ther. Targets*, vol. 13, No. 2, pp. 153-162 (2009).
Torisu et al., "Suppressor of Cytokine Signaling 1 Protects Mice Against Concanavalin A-Induced Hepatitis by Inhibiting Apoptosis, *Hepatology*, vol. 47, pp. 1644-1654 (2008).
Tupin et al., "The unique role of natural killer T cells in the response to microorganisms," *Nature Rev. Microbiology*, vol. 5, pp. 405-417 (2007).
Yu et al., "Modulation of CD1d-restricted NKT cell responses by using N-acyl variants of alpha-galactosylceramides," *PNAS*, vol. 102, No. 9, pp. 3383-3388 (2005).

(56) References Cited

OTHER PUBLICATIONS

Zajonc et al., "Structure and function of a potent agonist for the semi-invariant natural killer T cell receptor," *Nature Immunology*, vol. 6, No. 8, pp. 810-818 (2005).

Zigmund et al., "beta-Giucosylceramide: a novel method for enhancement of natural killer T lymphoycte plasticity in murine models of immune-mediated disorders," *Gut*, vol. 56, pp. 82-89 (2007).

Zigmund et al., "beta-Glycosphingolipids improve glucose intolerance and hepatic steatosis of the Cohen diabetic rat," *Am J Physiol Endocrinol Metab*, vol. 296, pp. E72-E78 (2009).

 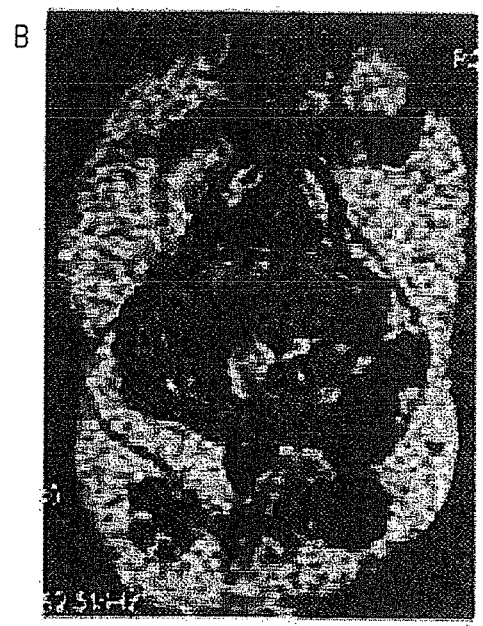
CONTROL OB/OB          GC-TREATED OB/OB
FIG. 16
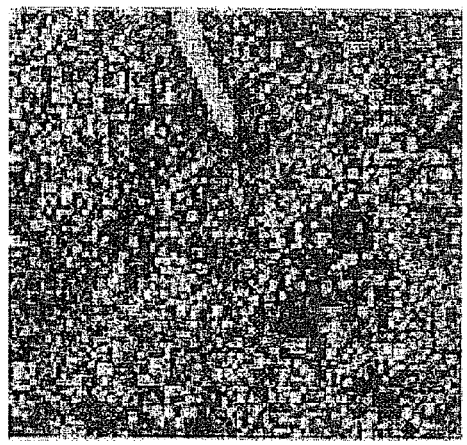 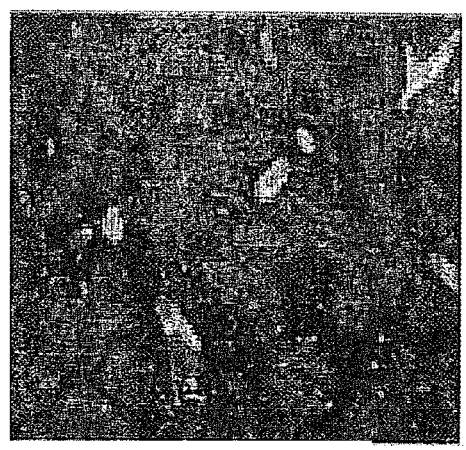
CONTROL OB/OB          GC-TREATED OB/OB
FIG. 17

GLUCOCEREBROSIDE TREATMENT OF LIVER DISORDERS

REFERENCE TO RELATED PATENT APPLICATIONS

This application is a continuation of U.S. patent application Ser. No. 11/378,941, filed on Mar. 17, 2006, which is a continuation-in-part of U.S. patent application Ser. No. 10/675,980, filed on Sep. 30, 2003, which is a continuation-in-part of U.S. patent application Ser. No. 10/375,906, filed on Feb. 27, 2003, now abandoned. The contents of the aforementioned patent applications are hereby incorporated by reference in their entireties.

FIELD OF THE INVENTION

This invention relates to the use of a naturally occurring, mammalian intermediary metabolite or T cell receptor ligand, preferably Glucocerebroside, for the treatment of liver disorders.

All patents, patent applications, patent publications, scientific articles, and the like, are hereby incorporated by reference in their entirety in order to describe more fully the state of the art to which the present invention pertains.

BACKGROUND OF THE INVENTION

Treatment of Immune Disorders

Various methods have been described for the treatment of immune-related or immune mediated disorders or diseases, infectious diseases, metabolic disorders and different types of cancer in mammalian subjects. One of these methods involves the modulation of immune responses in a subject. This includes the down regulation of the immune response system using procedures or combinations of procedures for producing and applying a new and unexpected immune modulation termed selective immune down regulation (SIDR). Immunological modulation is an artificially induced variation in a subject's immune system in response to the introduction of reagents, procedures and processes. These procedures have been described in detail in U.S. patent application Ser. No. 08/808,629, filed on Feb. 28, 1997, U.S. patent application Ser. No. 10/377,628, filed on Mar. 4, 2003, U.S. application Ser. No. 10/377,603, filed on Mar. 4, 2003, U.S. patent application Ser. No. 09/447,704, filed on Feb. 28, 1997, U.S. application Ser. No. 10/385,440, filed on May 9, 2001, and U.S. application Ser. No. 09/356,294, filed on Jul. 16, 1999. Each if the foregoing patents are incorporated by reference in their entirety in the present application and may further be used in conjunction with the present invention.

NKT Cells

Natural killer T (NKT) lymphocytes are a subset of regulatory lymphocytes that co-express cell surface receptors characteristic of both T lymphocytes (e.g. CD3, α/β T cell receptor) and natural killer cells (e.g. NK1.1) (Godfrey et al. 2000, Immunol Today 2000; 21: 573). In mice, most NKT cells express the invariant Vα14Jα281 TCR chain, paired with a limited number of β chain types (Vβ8.2, Vβ7, and Vβ2) (Bendelac et al., 1997, Annu. Rev. Immunol. 15:535-56). In humans, distinct populations of NKT cells express the homologous invariant Vα24 paired with Vβ11 (Kim et al., 2002, Trends Immunol 23: 516-19). NKT lymphocytes are activated by interaction of their TCR with glycolipids presented by CD1d, a nonpolymorphic, MHC class I-like molecule expressed by antigen presenting cells. CD1d is also expressed by hepatocytes (Bleicher et al., 1990, Science 250: 679-82). While a natural CD1d-bound ligand capable of activating NKT cells has not been identified in mammals, α-galactosylceramide (α-GalCer, KRN-7000), a sponge-derived glycolipid, is a potent activator of both mouse and human NKT cells (Kawano et al., 1997, Science 278:1626). Administration of α-GalCer leads to rapid production of both IFNγ and IL-4 by NKT cells, with secondary activation of innate and adaptive immune responses (Chen et al., 1997, J Immunol 159: 2240 and Taniguchi et al., 2003, Nat Immunol. 4:1164-5). NKT cells also recognize glycosylphosphatidylinositol (GPI) anchors of *Plasmodium, Trypanosoma* and *Leishmania*, and phosphatidylinositol-mannosides derived from *Mycobacterium tuberculosis* (Godfrey et al., 2000, Immunol Today 21: 573).

Furthermore, NKT lymphocytes, have a role in various infectious, inflammatory, and neoplastic processes (Vincent et al., 2003, Nature Immunol 2003; 4: 517). These cells, which are abundant in the liver, are considered to be a link between innate and adaptive immune responses (Bendelac et al., 1997, Curr Opin Immunol 9:1-3), and were shown to have a role in a number of immune-mediated disorders. In NOD mice, reduced numbers of NKT cells are associated with increased susceptibility to diabetes (Baxter et al., 1997, Diabetes 46:572-82); in experimental allergic encephalomyelitis, activation of NKT attenuates the disease (Miyamoto et al., 2001, Nature 2001:413:531-4); in an animal model of systemic lupus erythematosus, a selective reduction in NKT cells precedes the development of autoimmune phenomena (Takeda et al., 1993, J Exp Med 177:155-64). NKT cells are known to induce hepatic injury in several models, including concanavalin A (Takeda et al., 2000, Proc. Natl. Acad. Sci. USA 97: 5498-5503 and Eberl et al., 1998, Immunity 9:345-353) and *salmonella* infection-induced liver damage.

Leptin-deficient ob/ob mice feature a dysfunctional immune response, manifested by depletion of hepatic NKT lymphocytes and impaired function of hepatic Kupffer cells (Lee et al., 1999, Am J Physiol 276:c386-c394; Loffreda et al., 1998, FASEB J 1998; 12:57-65 and Li et al., 2002, Gastroenterology 2002, 123:1304-1310). These alterations may explain the relatively increased sensitivity to LPS-induced hepatotoxicity and resistance to concanavalin A-induced hepatitis and experimental allergic encephalomyelitis observed in these animals (Matarese et al., 2001, J Immunol 166:5909-16).

Activation of NKT lymphocytes can lead to significant liver damage (Ogasawara et al., 1998; 160, 3522-27 and Osman et al., 2000, Eur J Immunol 30: 191). Concanavalin A, a plant lectin and T cell mitogen, rapidly induces severe immune-mediated hepatitis in mice, that is associated with increased TNFα, IFNγ, IL-12, IL-18, and IL-4 expression (Siebler et al., 2003, Hepatology 38:1573-80) and in which NKT lymphocytes, CD4+ T cells and Kupffer cells have a contributory role (Schumann et al., 2000, Am J Pathol 157: 1671-83). Vα14 NKT cells were shown to be required and sufficient for induction of this type of liver injury (Kaneko et al., 2000, J Exp Med 191:105-14). The cytotoxic activity of NKT lymphocytes is augmented by autocrine secretion of IL-4, leading to increased expression of granzyme B and Fas ligand by NKT lymphocytes; Vα14 NKT cells from perforin knockout or FasL-mutant gld/gld mice fail to induce hepatitis. In another study, adoptive transfer of NKT cells from wild-type, but not from FasL-deficient gld mice, sensitized CD1-deficient mice, which lack NKT cells, to Con A-induced hepatitis (Takeda et al., 2000, Proc Natl Acad Sci USA 97:5498-503). NKT cells also have a central role in lipopolisaccharide (LPS), α-GalCer, and *salmonella* infection-induced liver injury (Takahashi et al., 1996, J Immunol 156: 2436-42; Nakagawa et al., 2001, J Immunol 166: 6578-84 and Ishigami et al, 1999, Hepatology 29:1799-808), in hepatic injury secondary to deletion of suppressor of cytokine signaling-1 (SOCS-1) (Naka et al., 2001 Immunity 14: 535-45), and in hepatic damage in the setting of chronic hepatitis C infection and primary biliary cirrhosis (Yonekura et al., 2000, Liver 20: 357-65 and Tsuneyama et al., 1998, Hepatology 28: 620-3).

Methods directed to the manipulation of the NKT cell population in a subject that results in the modulation of the Th1/Th2 balance toward anti-inflammatory or pro-inflammatory cytokine producing cells. A detailed description of these inventions have been disclosed in U.S. patent application entitled "Educated NKT Cells and Their Uses in the Treatment of Immune-Related Disorders" by Yaron Ilan et al., filed on Jun. 25, 2003 (application Ser. No. 10/451,811), PCT Application No. IL01/01197, filed on Dec. 24, 2001, and U.S. application Ser. No. 10/375,906, filed on Feb. 27, 2003.

NAFLD

Obesity is strongly associated with non-alcoholic fatty liver disease (NAFLD), ranging from simple steatosis to non-alcoholic steatohepatitis (NASH). Hepatic steatosis ("first hit") results from accumulation of lipids, predominantly triglycerides, within hepatocytes, due to variable combinations of excess lipid uptake and synthesis and altered lipid secretion. The transition from simple steatosis to NASH is thought to involve a "second hit", usually attributed to oxidative stress (Day et al., 1998, Gastroenterology 114: 842-5).

The pathogenesis of non-alcoholic steatohepatitis (NASH) may also involve a number of immune mechanisms. A number of immunological derangements have been noted in leptin-deficient ob/ob mice, a murine model for NASH. These include impaired cell-mediated immunity (Howard et al., 1999, J Clin Invest 1999, 104:1051-9 and Lord et al., 1998, Nature 394:897-901), a reduction in the number of intrahepatic NKT lymphocytes (Guebre-Xabier et al., 2000, Hepatology 31: 633-640), impaired function of hepatic Kupffer cells (Lee et al., 1999, Am J Physiol 276:c386-c394), reduced serum levels of IL-10 and IL15, and increased serum levels of IL-12 (Loffreda et al., 1998, FASEB J 12:57-65; Li et al., 2002, Gastroenterology 2002; 123:1304-1310 and Tilg et al., 2000, N Eng J Med 343: 1467-76). The reduced number of intrahepatic NKT lymphocytes in ob/ob mice may result from chronic oxidative stress that promotes increased apoptosis. Altered secretion of IL-15 by Kupffer cells, which is important for NKT cell differentiation, and decreased expression of leukocyte factor antigen 1 (LFA-1), necessary for hepatic accumulation of CD4+ NKT lymphocytes, were also suggested to be responsible for this defect (Kennedy et al., 2000, J Exp Med 191:771-780 and Takeda et al., 2000, Proc Natl Acad Sci USA 97:5498-5503). Leptin replenishment results in increased numbers of hepatic NKT lymphocytes, and partial reversal of the associated immune derangements in these animals.

At present, there is no effective therapy for NASH. Attempts have been made to target the underlying metabolic process by administration of a number of pharmacological agents, including vitamin E, metform in, pioglitazone, rosiglitazone, probucol and betaine (Brunt, 2004, Semin Liver Dis. 24:3-20), with variable effects on the hepatic fat content and serum aminotransferase levels. Current treatment approaches are directed primarily at achieving control of the metabolic conditions associated with NASH.

Glucocerebroside

Glucosylceramide is a naturally occurring glycolipid consisting of ceramide, to which glucose is attached. A ceramide, which is a sphingosine and a fatty acid, is the structural unit common to all sphingolipids. Sphingolipids have a variety of cellular functions. These include membrane structural roles and cell signaling participation. (Sullard et al., 2000 Journal of Mass Spectrometry 35:347-353.) Glucosylceramide is made by the enzyme glucosylceramide synthase which attaches the two molecules together (see FIG. 1 and FIG. 2). An example of a glucosylceramide includes glucocerebroside, or a glucocerebroside analogue or derivative. Mammalian glucocerbroside has a single trans double bond at position 4. Soy derived glucocerebroxide has two double bonds at positions 4 and 8 (65% trans, 35% cis) (Sullard et al., 2000, J Mass Spectrom 35:347-53).

The genetic disease Gaucher's Disease is characterized by an accumulation of glucosylceramide. In the treatment of this disorder by appropriate enzyme therapy, the excess glucosylceramide is degraded (Elstein et al., 2002, Paediatr Drugs 4:417-26). Two side effects of this treatment have been noted. In the course of this treatment, chronic active hepatitis associated with Hepatitis C virus infection was exacerbated. Additionally, certain patients (with pre-diabetic conditions) experienced the development of diabetic conditions, indicating an onset of Type II Diabetes. These observations further directly confirm that in human subjects, glucosylceramide levels regulate the onset of immune-mediated or immune-regulated disorders or diseases.

SUMMARY OF THE INVENTION

This invention relates to the use of one or more metabolic intermediates in the metabolic pathways of complex glycosphingolipids for treating a liver disorder. Specifically, the invention is directed to a method for modulating the amount of Natural Killer T (NKT) cells present in a mammalian subject, particularly a human being, in need thereof comprising administering to said subject an amount of one or more metabolic intermediates in the metabolic pathways of complex glycosphingolipids effective to modulate said amount of NKT cells.

In a related aspect, the invention relates to a method for modulating the amount of Natural Killer T (NKT) cells present in a mammalian subject in need thereof comprising administering to said subject an amount of one or more metabolic intermediates in the metabolic pathways of complex glycosphingolipids effective to modulate said amount of NKT cells. In a particular embodiment, the NKT cells are intrahepatic NKT cells. In yet another particular embodiment, the amount of NKT cells present in a subject are reduced, in particular at least about 15%.

In another related aspect the invention relates to a method for modulating cytokine levels in a mammalian subject in need thereof comprising administering to said subject an amount of a metabolic intermediate in the metabolic pathways of complex glycosphingolipids effective to modulate said cytokine levels. Examples of cytokines that may be modulated include but are not limited to interferon-gamma, interleukin 10, (IL-10), interleukin 2 (IL-2) and/or interleukin 12 (IL-12). In one embodiment, the level of interferon-gamma is reduced and/or interleukin 10 is increased. In a specific embodiment, the level of interferon-gamma is decreased at least about 30% and the level of interleukin 10 is increased at least about 2.5 fold. In another embodiment, the level of interferon-gamma is decreased, interleukin 10 is decreased, interleukin 2 is increased and/or interleukin 12 is increased. In another particular embodiment, the level of level of interferon-gamma is decreased at least about 30, the level of interleukin 10 is decreased at least about 3.5 fold, the level of interleukin 12 is increased at least about two fold, the level of interleukin 2 is increased about 2 fold.

In yet another related aspect, the invention relates to a method for modulating one or more transcription factors including but not limited to STAT 1 (signal transducer of activation 1), STAT 4, and/or STAT 6 in a mammalian subject in need thereof comprising administering to said subject an amount of one or more metabolic intermediates in the metabolic pathways of complex glycosphingolipids effective to modulate said levels of transcription factor. In a particular embodiment, the level of STAT 1 is decreased, the level of STAT 4 is increased and/or the level of STAT 6 is increased.

In a further related aspect, the invention relates to a method for increasing the peripheral/intrahepatic T cell ratio at least 1.5 fold in a mammalian subject in need thereof comprising administering to said subject an amount of one or more metabolic intermediates in the metabolic pathways of complex glycosphingolipids effective to increase said intrahepatic/peripheral T cell ratio.

In another further related aspect, the invention relates to a method for modulating the level of alanine aminotransferase (ALT) and aspartate aminotransferase (AST) present in the serum of a mammalian subject in need thereof comprising administering to said subject an amount of one or more metabolic intermediates in the metabolic pathways of complex glycosphingolipids effective to modulate said ALT and AST level. In a particular embodiment, serum ALT and AST levels are decreased, in particular decreased at least about four fold.

Another aspect of the present invention provides for the treatment of a disease in a mammalian subject comprising the ex vivo treating or educating of cells obtained from the mammalian subject. The cells are treated or educated with an effective amount of the intermediary metabolite.

The invention is also directed to a method for diagnosing a liver disease or disorder in a subject comprising isolating a serum sample from a subject, assaying for the level of ALT, AST, IFN-gamma, STAT 1 and/or IL-10 present in said sample and comparing the level of these substances in the sample with levels of these substances present in a disease free subject. An increased level of ALT, AST, IFN-gamma, STAT 1 and/or IL-10 and/or decreased level of STAT 4, STAT 6, IL-2 and/or IL-12 in a serum sample from a subject compared to a subject free of said liver disease or disorder may indicate the presence of a liver disease or disorder, particularly immune-mediated hepatitis in said subject. A decreased level of IL-10 and/or increased level of IFN-gamma in a subject relative to a subject free of liver disease may indicate the presence of a liver disease or disorder such as nonalcoholic fatty liver disease.

The invention is directed to a method for monitoring the treatment of a liver disorder in a mammalian subject undergoing said treatment comprising isolating a serum sample from a subject and determining periodically the level of ALT, AST, IL-10, IL-2, IL-12, IFN-gamma, STAT 1, STAT 4, STAT 6 in said subject using procedures known in the art, embodiments of which are described in the Examples below. The subject may be monitored daily, weekly or monthly. A decrease in ALT, AST, IFN-gamma, STAT 1 and/or IL-10 and increase in STAT 4, STAT 6, IL-2 and/or IL-12 in a sample from a subject with the liver disease or disorder such as hepatitis indicates progress in treatment of treatment of a liver disorder such as hepatitis, particularly, immune mediated hepatitis. A decrease in IFN-gamma and increase in IL-10 may indicate in a serum sample from a subject indicates progress in the treatment of a liver disorder such as non alcoholic fatty liver disease.

The invention is further directed to a method for treating a glucose metabolism disease or disorder in a mammalian subject in need thereof comprising administering to said subject an amount of one or more metabolic intermediates in the metabolic pathways of complex glycosphingolipids in an amount effective for treating said glucose metabolism disease of disorder. The disease or disorder includes but is not limited to obesity, Diabetes Mellitus, and glucose intolerance.

In a related aspect, the invention is directed to a method for diagnosing a glucose metabolism disease or disorder comprising isolating a serum sample from a subject and assaying for the level of IFN-gamma, and/or IL-10 present in said sample. A decreased level of IL-10 and/or increased level of IFN-gamma in the subject compared to a subject free of said glucose metabolism disease or disorder may indicate the presence of a glucose metabolism disease or disorder such as glucose intolerance. This may be used in conjunction with other tests currently known such as glucose tolerance tests.

In a further related aspect, the invention is directed to a method for monitoring the treatment of a glucose metabolism disease or disorder in a mammalian subject undergoing said treatment (e.g., treatment with one or more metabolic intermediates in the metabolic pathways of complex glycosphingolipids) comprising isolating a serum sample from a subject and determining periodically the level of IL-10 and/or IFN-gamma, in said subject using procedures known in the art, embodiments of which are described in the Examples below. The subject may be monitored daily, weekly or monthly. A decrease in IFN-gamma and/or increase in IL-10 may indicate in a serum sample from a subject indicates progress in the treatment of a glucose metabolism disease or disorder.

BRIEF DESCRIPTION OF THE FIGURES

FIG. 16 shows the effect of glucocerebroside on hepatic fat content.

> MRI images depicting reduced sized liver with low SI index of 0.08 (A, asterisk marking the liver); enlarged ob/ob liver of control group B with elevated SI index of 0.63 (B, double asterisk marking the liver).

FIG. 17 shows the histological examination of livers of glucocerebroside-treated ob/ob mice (group A) compared to control ob/ob mice (group B).

Figure 18:
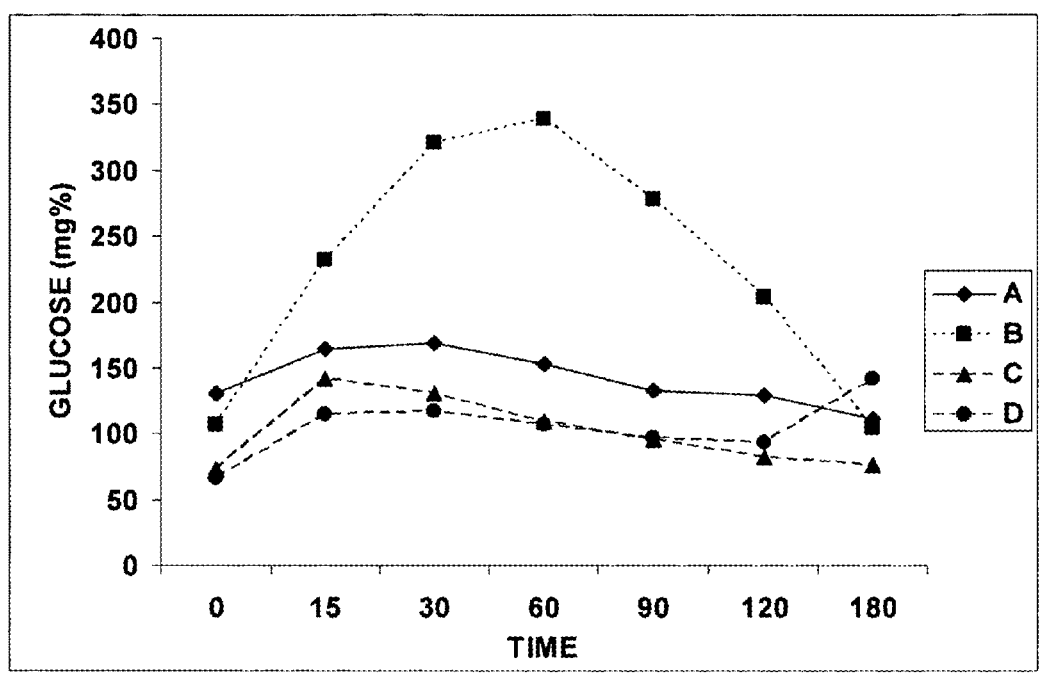

FIG. 18 shows the effect of glucocerebroside on glucose tolerance in GC treated ob/ob mice (group A) and untreated ob/ob mice (group B).

Figure 19:
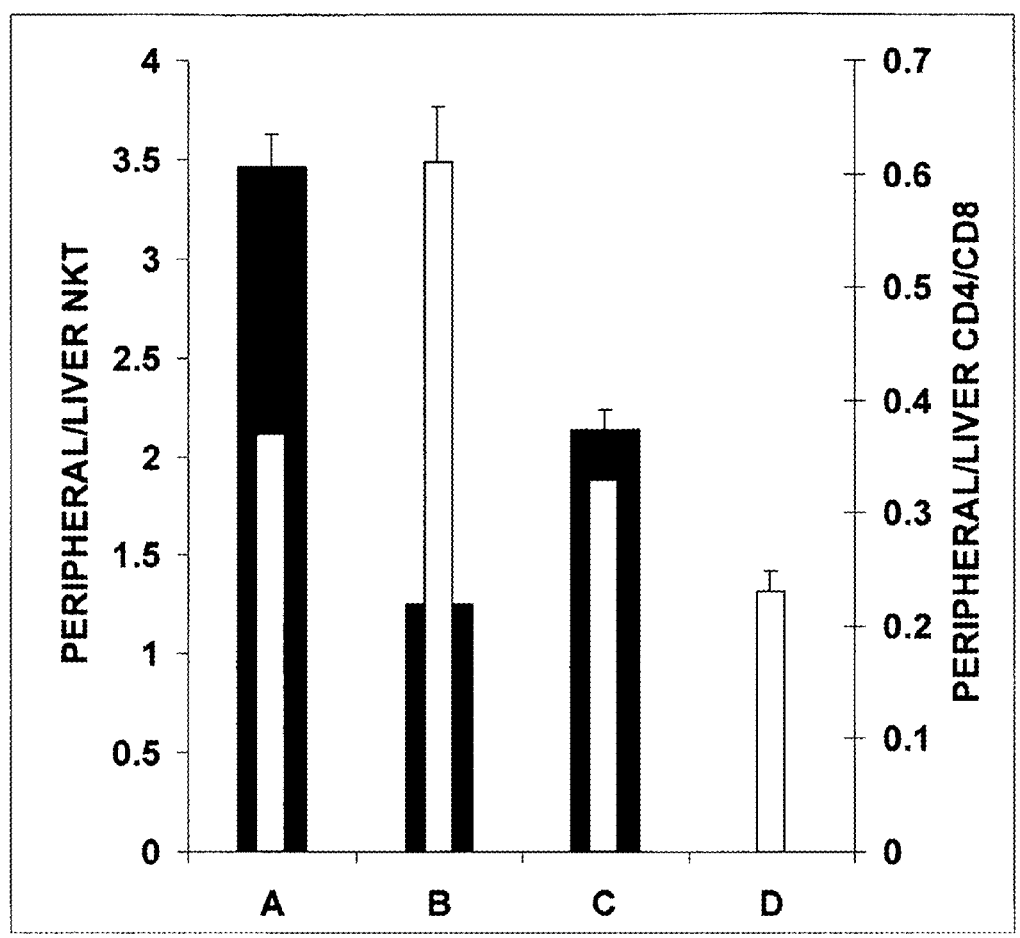

FIG. 19 shows the effect of glucocerebroside on intrahepatic and intrasplenic lymphocyte subsets. Peripheral/intrahepatic NKT lymphocyte ratio is depicted in black bars for glucocerebroside-treated ob/ob mice (group A mice) and lean mice (group C) compared to controls (group B (untreated ob/ob) and D (untreated lean) mice). Intrahepatic CD4+/CD8+ lymphocyte ratio is depicted in open bars for the GC treated group (groups A and C as above) compared to non treated controls (groups B and D as above).

Figure 20:
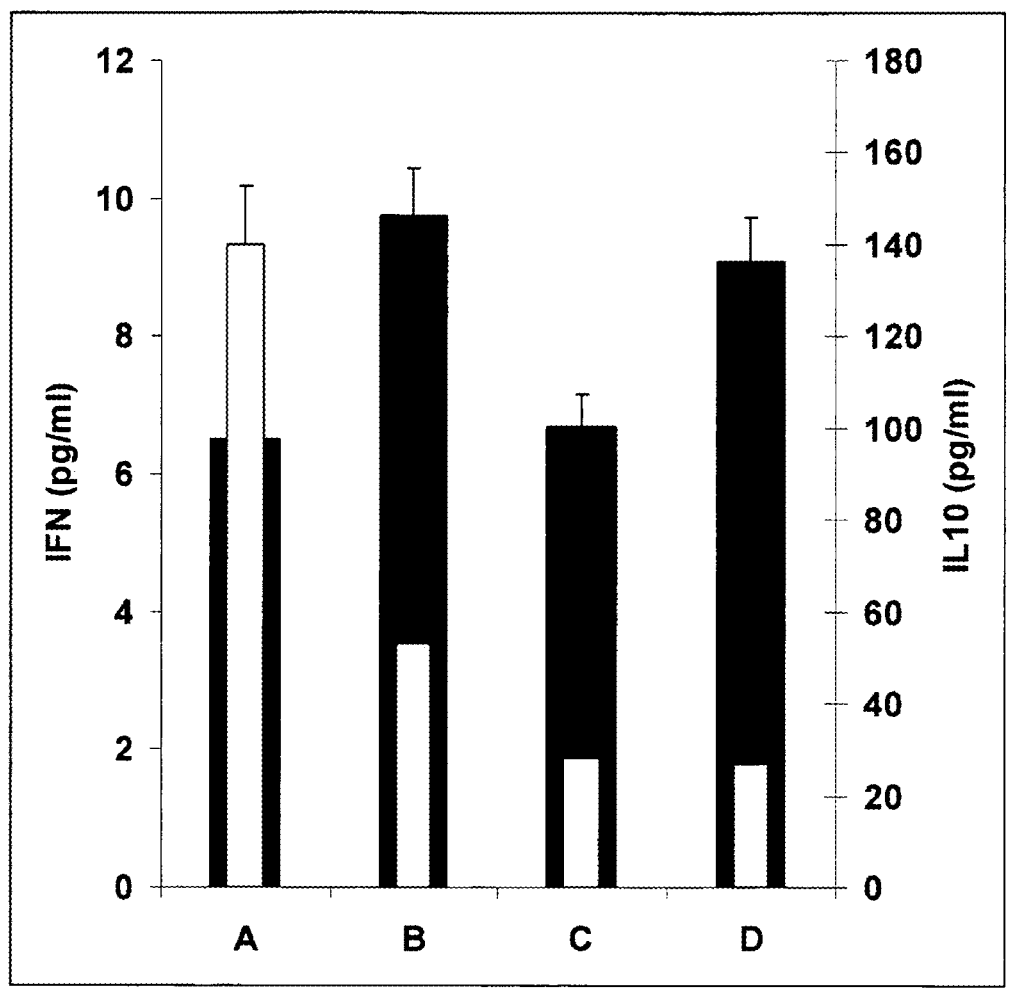

FIG. 20 shows the effect of adoptive transfer of NKT lymphocytes on serum cytokine levels: A 33% decrease of the serum IFNγ level (black bars) and a 2.6 time fold increase of the serum IL-10 (open bars) were noted in glucocerebroside-treated ob/ob mice (group A) compared to control ob/ob mice (group B).

DETAILED DESCRIPTION OF THE INVENTION

The terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

The present invention provides methods for the treatment of a liver disease (e.g. hepatitis, particularly immune-mediated hepatitis or non-fatty lipid disease) or glucose metabolism disease or disorder (e.g., glucose intolerance, diabetes, obesity) in a mammalian subject by the administration of an effective amount of one or more metabolic intermediates in the metabolic pathways of complex glycosphingolipids to the subject. The metabolic intermediate includes, but is not limited to a T cell receptor ligand, a lipid, a polar lipid, a conjugated biomolecule, a glycolipid, a lipoprotein, an apolipoprotein, a glycoprotein, a monosaccharide or polysaccharide ceramide, a glucosylceramide, a galactosylceramide, a glucocerebroside, a glucocerebroside analogue or derivative, a sphingosine, a sphingolipid or a ceramide. In a particular embodiment, the glucocerebroside is soy-derived glucocerebroside. In a preferred embodiment of the invention, the mammalian subject is a human being.

The intermediate metabolites of the present invention (e.g., glucocerebroside) may be introduced directly to the subject using methods known in the art (see, for example, Rolland, 1998, Crit. Rev. Therap. Drug Carrier Systems 15:143-198 and references cited therein and Ulmer, 1993, Science 259:1745-1749). Methods include but are not limited to the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN" and LIPOFECTACE", which are formed of cationic lipids such as N—[I-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art. Alternatively, the intermediate metabolite may be added to intrahepatic NKT cells ex vivo obtained from said patient and said treated cells may be subsequently readministered to the subject.

In another embodiment of the therapeutic methods of the present invention, a therapeutically effective amount of a pharmaceutical composition comprising the intermediate metabolite(s) of the present invention is administered. Such a composition typically contains from about 0.1 to 90% by weight of a metabolic intermediate of the invention formulated in and/or with a pharmaceutically acceptable carrier or excipient. Pharmaceutical formulation is a well-established art, and is further described in Gennaro (ed.), Remington: The Science and Practice of Pharmacy, 20th ed., Lippincott, Williams & Wilkins (2000); Ansel et al., Pharmaceutical Dosage Forms and Drug Delivery Systems, 7th ed., Lippincott Williams & Wilkins (1999); and Kibbe (ed.), Handbook of Pharmaceutical Excipients American Pharmaceutical Association, 3rd ed. (2000).

Briefly, formulation of the pharmaceutical compositions of the present invention will depend upon the route chosen for administration. The pharmaceutical compositions utilized in this invention can be administered by various routes including both enteral and parenteral routes, including oral, intravenous, intramuscular, subcutaneous, inhalation, intrathecal, intraventricular, transmucosal, transdermal, intranasal, intraperitoneal, and intrapulmonary. The pharmaceutical composition may comprise one or more agents of the present invention.

Oral dosage forms can be formulated as tablets, pills, dragees, capsules, liquids, gels, syrups, slurries, suspensions, and the like, for ingestion by the patient. Solid formulations of the compositions for oral administration can contain suitable carriers or excipients, such as carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; and other agents such as acacia and alginic acid. Agents that facilitate disintegration and/or solubilization can be added, such as the cross-linked polyvinyl pyrrolidone, agar, alginic acid, or a salt thereof, such as sodium alginate, microcrystalline cellulose, corn starch, sodium starch glycolate, and alginic acid. Tablet binders that can be used include acacia, methylcellulose, carboxymethylcellulose, polyvinylpyrrolidone (Povidon™) hydroxypropyl methylcellulose, sucrose, starch and ethylcellulose. Lubricants that can be used include magnesium stearates, stearic acid, silicone fluid, talc, waxes, oils, and colloidal silica. Fillers, agents that facilitate disintegration and/or solubilization, tablet binders and lubricants, including the aforementioned, can be used singly or in combination. Solid oral dosage forms need not be uniform throughout. For example, dragee cores can be used in conjunction with suitable coatings, such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures.

Oral dosage forms of the present invention include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers. Additionally, dyestuffs or pigments can be added to the tablets or dragee coatings for product identification or to characterize the quantity of active compound, i.e., dosage.

Liquid formulations of the pharmaceutical compositions for oral (enteral) administration are prepared in water or other aqueous vehicles and can contain various suspending agents such as methylcellulose, alginates, tragacanth, pectin, kelgin, carrageenan, acacia, polyvinylpyrrolidone, and polyvinyl alcohol. The liquid formulations can also include solutions, emulsions, syrups and elixirs containing, together with the active compound(s), wetting agents, sweeteners, and coloring and flavoring agents.

The pharmaceutical compositions of the present invention can also be formulated for parenteral administration. Formulations for parenteral administration can be in the form of aqueous or non-aqueous isotonic sterile injection solutions or suspensions.

For intravenous injection, water soluble versions of the compounds of the present invention are formulated in, or if provided as a lyophilate, mixed with, a physiologically acceptable fluid vehicle, such as 5% dextrose ("D5"), physiologically buffered saline, 0.9% saline, Hanks' solution, or Ringer's solution. Intravenous formulations may include carriers, excipients or stabilizers including, without limitation, calcium, human serum albumin, citrate, acetate, calcium chloride, carbonate, and other salts.

Intramuscular preparations, e.g. a sterile formulation of a suitable soluble salt form of the compounds of the present invention, can be dissolved and administered in a pharmaceutical excipient such as Water-for-Injection, 0.9% saline, or 5% glucose solution. Alternatively, a suitable insoluble form of the compound can be prepared and administered as a suspension in an aqueous base or a pharmaceutically acceptable oil base, such as an ester of a long chain fatty acid (e.g., ethyl oleate), fatty oils such as sesame oil, triglycerides, or liposomes.

Parenteral formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like).

Aqueous injection suspensions can also contain substances that increase the viscosity of the suspension, such as sodium carboxymethyl cellulose, sorbitol, or dextran. Non-lipid polycationic amino polymers can also be used for delivery. Optionally, the suspension can also contain suitable stabilizers or agents that increase the solubility of the compounds to allow for the preparation of highly concentrated solutions.

Pharmaceutical compositions of the present invention can also be formulated to permit injectable, long-term, deposition. Injectable depot forms may be made by forming microencapsulated matrices of the compound in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in microemulsions that are compatible with body tissues.

Inhalation formulations can also readily be formulated. For inhalation, various powder and liquid formulations can be prepared. For aerosol preparations, a sterile formulation of the compound or salt form of the compound may be used in inhalers, such as metered dose inhalers, and nebulizers. Aerosolized forms may be especially useful for treating respiratory disorders.

Alternatively, the compounds of the present invention can be in powder form for reconstitution in the appropriate pharmaceutically acceptable carrier at the time of delivery.

The pharmaceutically active compound in the pharmaceutical compositions of the present invention can be provided as the salt of a variety of acids, including but not limited to hydrochloric, sulfuric, acetic, lactic, tartaric, malic, and succinic acid. Salts tend to be more soluble in aqueous or other protonic solvents than are the corresponding free base forms.

After pharmaceutical compositions have been prepared, they are packaged in an appropriate container and labeled for treatment of an indicated condition.

The active compound will be present in an amount effective to achieve the intended purpose. The determination of an effective dose is well within the capability of those skilled in the art.

The therapeutically effective dose of the pharmaceutical metabolic intermediates of the present invention can be estimated initially by in vitro tests, such as cell culture assays, followed by assay in model animals, usually mice, rats, rabbits, dogs, or pigs. The animal model can also be used to determine an initial preferred concentration range and route of administration.

For example, the $ED_{50}$ (the dose therapeutically effective in 50% of the population) and $LD_{50}$ (the dose lethal to 50% of the population) can be determined in one or more cell culture of animal model systems. The dose ratio of toxic to therapeutic effects is the therapeutic index, which can be expressed as $LD_{50}/ED_{50}$. Pharmaceutical compositions that exhibit large therapeutic indices are preferred.

The data obtained from cell culture assays and animal studies are used in formulating an initial dosage range for human use, and preferably provide a range of circulating concentrations that includes the $ED_{50}$ with little or no toxicity. After administration, or between successive administrations, the circulating concentration of active agent varies within this range depending upon pharmacokinetic factors well known in the art, such as the dosage form employed, sensitivity of the patient, and the route of administration.

The exact dosage will be determined by the practitioner, in light of factors specific to the subject requiring treatment. Factors that can be taken into account by the practitioner include the severity of the disease state, general health of the subject, age, weight, gender of the subject, diet, time and frequency of administration, drug combination(s), reaction sensitivities, and tolerance/response to therapy. Long-acting pharmaceutical compositions can be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. In a particular embodiment, the daily dosage is about 0.01 mg to 30 mg/kg of body weight of the patient (e.g., 1 mg/kg to 5 mg/kg). The pharmaceutical formulation can be administered in multiple doses per day, if desired, to achieve the total desired daily dose.

Conventional methods, known to those of ordinary skill in the art of medicine, can be used to administer the pharmaceutical formulation(s) of the present invention to the patient. The pharmaceutical compositions of the present invention can be administered alone, or in combination with other therapeutic agents or interventions. Specifically, the compositions of the present invention may further comprise a plurality of agents of the present invention.

The treatment of a disease in any of the described methods results in a change in the number or function of regulatory, immune-regulatory or NKT cells. This change encompasses a reduction, inhibition, or decrease in the number or function of the cells. This inhibition may be caused by the competitive displacement of activating elements from the CD1d molecule. A change may also include a stimulation or increase in the number or function of the cells. This stimulation may be caused by increased binding of the activating elements from the CD1d molecule.

The treatment of a disease may also result in a change the cytokine responses. Any cytokine in the immune system may be involved in these responses. The change could result in a pro-inflammatory or an anti-inflammatory response. There may also be a pro-inflammatory, and an anti-inflammatory response since certain cytokines may increase and others may decrease, simultaneously.

Another result of the treatment of a disease is an alteration of the regulatory, immune-regulatory or NKT cell distribution in the subject. This change may also be accompanied by a change in the peripheral/intrahepatic T cell ratio. A further result may also include a change in intrahepatic CD8+ T cell trapping. There may be an increase or a decrease in the intrahepatic trapping. The result may also include a change in intrasplenic T cell trapping, where said change could be an increase or decrease.

In a preferred embodiment of the present invention, there is minimal interference with digestion and absorption of metabolic intermediates in the metabolic pathways of complex glycosphingolipids, or analog or derivative thereof, a lipid, conjugated biomolecule, polar lipid, glycolipid, lipoprotein, apolipoprotein, cytokines or hormones, monosaccharide ceramide, glucosylceramide, galactosylceramide, glucocereboside, glucocereboside analogue or derivative, sphingosine, sphingolipid, ceramide, T cell ligand, T cell receptor ligand, a T cell receptor ligand analogue or derivative, or a glycoprotein other than an antibody, in the mammalian subject. Specifically, the mammalian subject has been without food and/or water for a certain amount of hours prior to the administration of the aforesaid molecules, treatment of the mammalian subject or the manipulation of cells in the mammalian subject. In a specific embodiment, the mammalian subject is subjected to fasting for a minimum of twelve hours prior to the administration of the metabolic intermediate.

The invention also provides a method for diagnosing a liver disease or disorder (e.g., hepatitis) or glucose metabolism disease or disorder in a subject. This method involves obtaining a serum sample from the subject; measuring the level of IFN-gamma, ALT, AST, IL-10, IL-2, IL-12, STAT 1, STAT 4 and/or STAT 6 in the sample. The level of IFN-gamma, ALT, AST, IL-10, IL-2, IL-12, STAT 1, STAT 4 and/or STAT 6 present in the sample is compared to the level of IFN-gamma, ALT, AST, IL-10, IL-2, IL-12, STAT 1, STAT 4 and/or STAT 6 present in a sample from a subject free of the glucose metabolism disease or disorder and/or liver disease or disorder. If the subject has such a liver disease or disorder such as hepatitis, particularly immune-mediated hepatitis, the sample from the subject suspected of having said disease will have an increased level of IFN gamma, IL-10, ALT, AST and/or STAT-1 is increased compared to the level of IFN-gamma IL-10, ALT, AST and/or STAT-1 present in the sample of a disease free subject. In a particular embodiment, the levels of these substances are increased. If the subject has such a liver disease or disorder such as non-alcoholic fatty liver disease or glucose metabolism disorder or disease, the sample from the subject suspected of having said disease will have an increased level of IFN-gamma and/or increased level of IL-1 compared to the level of these substances present in the sample of a disease-free subject. Methods for assaying IFN-gamma, ALT, AST, IL-10, IL-2, IL-12, STAT 1, STAT 4 and/or STAT 6 are known in the art and are described in the Examples herein below.

The invention also provides a method for monitoring the progress of treatment of a liver disease or disorder or glucose metabolism disease or disorder. If the disease is hepatitis or immune-mediated hepatitis, such a method comprises obtaining a serum sample from a subject before, during and after treatment and measuring levels of ALT, AST, IL-10, IFN-gamma, STAT 1, STAT 4, and/or STAT 6 in said subject. The subject may be monitored daily, weekly or monthly. If treatment is effective, the levels of IFN-gamma, ALT, AST, IL-10, and/or STAT 1 will be decreased. IL-2, IL-12, STAT 4 and/or STAT 6 will be increased. If the disease or disorder is non-alcoholic fatty liver disease or glucose metabolism disease or disorder, the levels of IFN-gamma will be decreased and/or IL-10 will be increased if treatment is effective; this assay may also be coupled with monitoring triglyceride levels and conducting glucose tolerance tests in said subjects.

The methods for carrying out the invention, and the experimental results which support and further explain the results obtained are as follows:

Examples

I. Glucocerebroside Treatment of Concanavalin-A Hepatitis
Materials and Methods
Preparation of Glycolipids β-Glucosylceramide was purchased from Avanti Polar Lipids (Alabaster, Ala.; Catalogue #131304), dissolved in ethanol and emulsified in PBS.

In Vitro Effect of Glucocerebroside

NKT lymphocytes and dendritic cells were isolated from spleens of naïve mice as described below. Harvested NKT lymphocytes were placed in 24 well plates. Naïve NKT lymphocytes ($1\times10^6$/well) were incubated for 24 hours in medium with or without glucocerebroside (100 ng/ml), in the presence or absence of dendritic cells ($1\times10^4$/well). Data is presented as mean stimulation indices (SI) of triplicates, calculated from the ratios of incorporated radioactivities in the presence or absence of antigen.

Radiolabeled GC

To determine the tissue distribution of GC, four groups of mice (a-d, n=2 per group) were administered radiolabeled GC (Avanti Polar Lipids, Alabaster, Ala.), orally (10 µg/mouse, groups a and c) or by a single intraperitoneal injection (1 µg/mouse, groups b and d). Group A and B animals were sacrificed after 2 hours; group c and d animals were sacrificed after 48 hours. Brain, liver, heart, lung, kidney, spleen, small intestine and colon were removed and homogenized in double-distilled water. Radioactivity per 100 mg tissue, expressed as cpm, was determined by a liquid scintillation analyzer (Opti-Flour, Packard, USA).

Animals

Eight week old male Balb/c mice were obtained from Jackson Laboratories (Bar Harbor, Me., USA) and maintained in the Animal Core of the Hadassah-Hebrew University Medical School. Mice were administered standard laboratory chow and water ad libitum, and kept in 12-hour light/dark cycles. Animal experiments were carried out according to the guidelines of the Hebrew University-Hadassah Institutional Committee for Care and Use of Laboratory Animals, and with the committee's approval.

Induction of Con A Hepatitis

Con A (Sigma) was dissolved in pyrogen-free PBS and injected into the tail vein at a dose of 500 µg/mouse (approximately 15 mg/kg).

Experimental Groups

Three ConA injected groups (A-C) and two non-injected groups (D,E) of Balb/c mice, 12 mice per group, were studied (Table 1).

TABLE 1

Experimental groups:

| Group: | ConA | GC |
|---|---|---|
| A | + | + (2 hours before ConA) |
| B | + | + (2 hours after ConA) |
| C | + | − |
| D | − | + |
| E | − | − |

Group A mice were administered a single intraperitoneal injection of glucocerebroside (1 µg GC in 100 µl PBS) 2 hours prior to IV administration of ConA. Group B mice were similarly injected with GC 2 hours after IV administration of ConA. Group C mice were administered ConA. Group D mice were treated with GC. Group E mice were not administered ConA or GC. Group B-E animals were sacrificed after eight hours; group A animals were sacrificed after 10 hours (8 hours after injection of ConA). For all animals, determination of serum aspartate aminotransferase (AST) and alanine aminotransferase (ALT) levels, histological examination of liver specimens, FACS analysis of intrahepatic and intrasplenic lymphocytes for NKT markers (CD3 and DX5), measurement of serum cytokine levels and western blot analysis for the expression of the transcription factors STAT 1,4 and 6 and NFκB were performed.

Liver Enzymes

Sera from individual mice were obtained. Serum AST and ALT levels were measured by an automatic analyzer.

Histological Examination

Hematoxylin/eosin staining of paraffin-embedded liver sections was performed. Sections were examined by two experienced pathologists that were blinded to the experiment conditions.

Cytokine Measurement

Serum IFNγ, IL-2, IL-12, IL-4 and IL-10 levels were measured in each animal by "sandwich" ELISA, using commercial kits (Genzyme Diagnostics, MA, USA).

Isolation of Splenocytes and Intrahepatic Lymphocytes

Splenocytes and intrahepatic lymphocytes were isolated as previously described (Trop et al., 1999, Hepatology 29:746-55). In brief, after flushing of the liver with cold PBS and removal of connective tissue, livers and spleens were crushed through a stainless mesh (size 60, Sigma Chemical Co., St. Louis Mo.). Cell suspensions in PBS were centrifuged (1250×rpm for 10 minutes) for removal of debris, and placed through a nylon mesh presoaked in PBS. Unbound cells were collected and 20 ml of histopague 1077 (Sigma Diagnostics, St. Louis, Mo.) were slowly placed under the cells; after centrifugation (1,640×rpm for 15 minutes at room temperature) cells at the interface were collected and washed twice. Approximately $1\times10^6$ cells/mouse liver were recovered. Viability was determined to be >95% by trypan blue staining.

STAT Protein Expression

Expression of the transcription factors STAT (signal transducer and activator of transcription) 1,4 and 6 and NFκB in splenocytes was determined by western blot analysis of splenocytes harvested from mice in groups A-D. Splenocytes ($10\times10^6$) were lysed in 100 µl of lysis solution (Sigma). Proteins (100 µg/lane) were resolved by electrophoresis on SDS-polyacrylamide (7.5%) gels, and electroblotted to nitrocellulose membranes (Schleicher & Scuell, Germany). Probing with a polyclonal rabbit anti-mouse antibody for the different tested STAT proteins and NFκB (Santa Cruz Biothechnology) was followed by addition of horseradish peroxidase-conjugated goat anti-rabbit IgG (Jackson Immuno Research, PA, USA).

FACS Analysis for Determination of NKT Lymphocyte Percentage

Immediately after lymphocyte isolation, triplicates of $2-5\times10^4$ cells/500 µl PBS were placed into Falcon 2052 tubes, incubated with 4 ml of 1% BSA for 10 minutes, and centrifuged at 1400 rpm for 5 minutes. For determination of the percentage of NKT lymphocytes, anti-CD3 and anti DX5 antibodies were used (Pharmingen, USA). Analytical cell sorting was performed on $1\times10^4$ cells from each group with a fluorescence-activated cell sorter (FACSTAR plus, Becton Dickinson). Only live cells were counted, and background fluorescence from non-antibody-treated lymphocytes was subtracted. Gates were set on forward- and side-scatters to exclude dead cells and red blood cells. Data was analyzed with the Consort 30 two-color contour plot program (Becton Dickinson, Oxnard, Calif.), or the CELLQuest 25 program.

Isolation of NKT Lymphocytes and Dendritic Cells

Cell separation was performed using Magnetic Cell Sorting (MACS, Miltenyi Biotec, Germany) according to the manufacturer's instructions. Anti-CD3 and anti-DX5 magnetic beads were used for separation of NKT lymphocytes; anti-CD11c beads served for separation of dendritic cells.

Statistical Analysis

Statistical analysis was performed using the student t test. P<0.05 was considered significant.

Results

Figure 1:
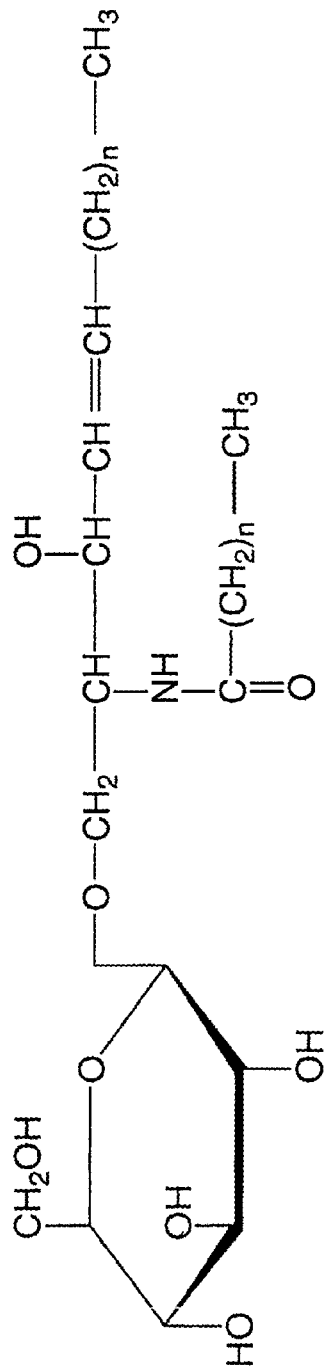
FIG. 1 shows the chemical structure of Glucocerebroside.
Figure 2:
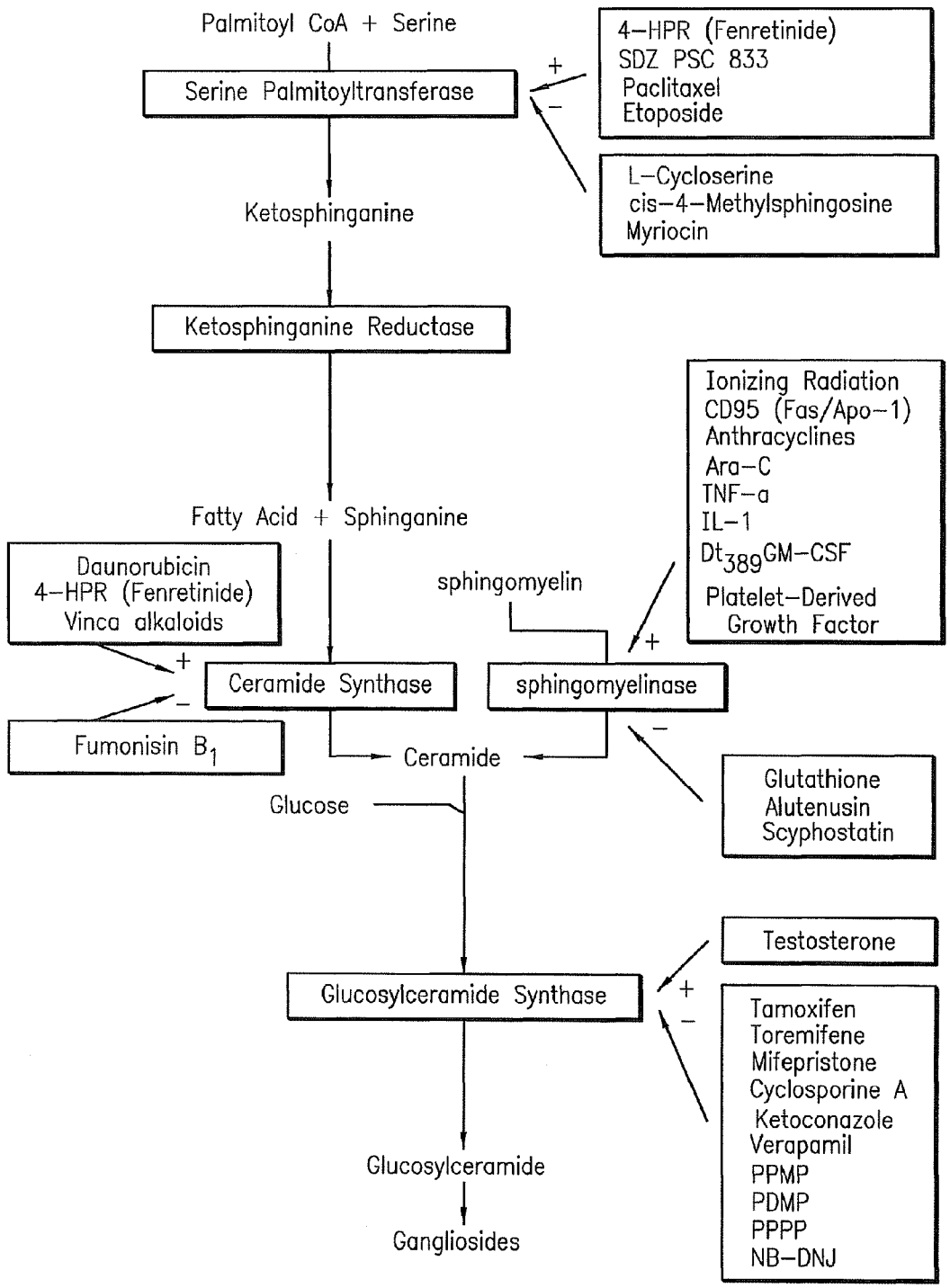
FIG. 2 shows the pathway to Glucosylceramide synthesis.
Figure 3:
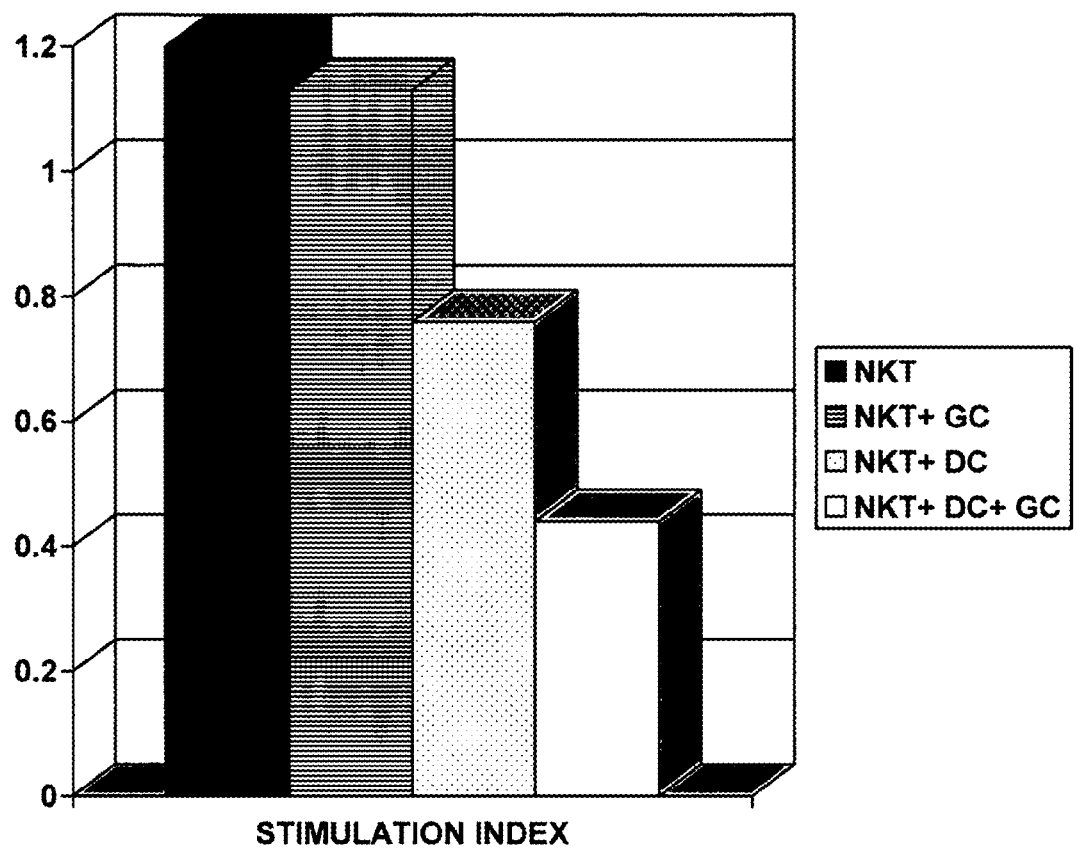
FIG. 3 shows the effect of glucocerebroside (GC) on NKT cell proliferation in vitro in the presence and absence of dendritic cells (DC).

Effect of Glucocerebroside on NKT Cell Proliferation In Vitro (FIG. 3)

The effect of incubation with GC on NKT cell proliferation was examined in vitro. Incubation of NKT lymphocytes with glucocerebroside did not affect NKT cell proliferation significantly (SI 1.2 vs. 1.13 in the absence and presence of glucocerebroside, respectively). In contrast, in the presence of dendritic cells, NKT cell proliferation was markedly inhibited by glucocerebroside (SI 0.44). This finding supports a role for antigen presentation in the inhibitory effect of glucocerebroside. Interestingly, the mere presence of dendritic cells was also found to inhibit NKT cell proliferation (SI 0.76).

In Vivo Distribution of Radiolabeled Glucocerebroside (Table 2):

Tissue distribution of radiolabeled glucocerebroside was examined twenty four and forty eight hours after intraperitoneal or oral administration. The results are shown below in Table 2:

TABLE 2

Distribution of radiolabeled glucocerebroside 24 and 48 hours after oral or intraperitoneal administration (cpm/100 mg tissue):

|  | ORAL | | INTRA-PERITONEAL | |
| --- | --- | --- | --- | --- |
|  | 24 h | 48 h | 24 h | 48 h |
| Brain | 37 | 26 | 33 | 39 |
| Heart | 108 | 54 | 64 | 33 |
| Lungs | 79 | 21 | 162 | 63 |
| Liver | 765 | 65 | 1164 | 369 |
| Spleen | 79 | 52 | 627 | 468 |
| Large bowel | 247 | 83 | 848 | 1017 |
| Small bowel | 609 | 296 | 1264 | 784 |
| Kidney | 255 | 74 | 407 | 212 |

After 24 hours, increased radioactivity levels were detected in the liver, small intestine, kidney and colon (765, 609, 255 and 247 cpms, respectively, after oral administration; 1164, 848, 407 and 1264 cpms, respectively, after intraperitoneal administration); radioactivity levels were also increased in the same tissues after 48 hours (65, 296, 74, 83 cpms for liver, small intestine, kidney and colon, respectively, after oral administration; 369, 784, 212 and 1017 cpms, respectively, after intraperitoneal administration). Spleen radioactivity was relatively high (627 and 468 cpms after 24 and 48 hours, respectively) after intraperitoneal administration of radioactive GC, but not after its oral administration. Radioactivity levels were relatively low in brain, lung and heart specimens after both oral and intraperitoneal administration of GC.

Figure 4:
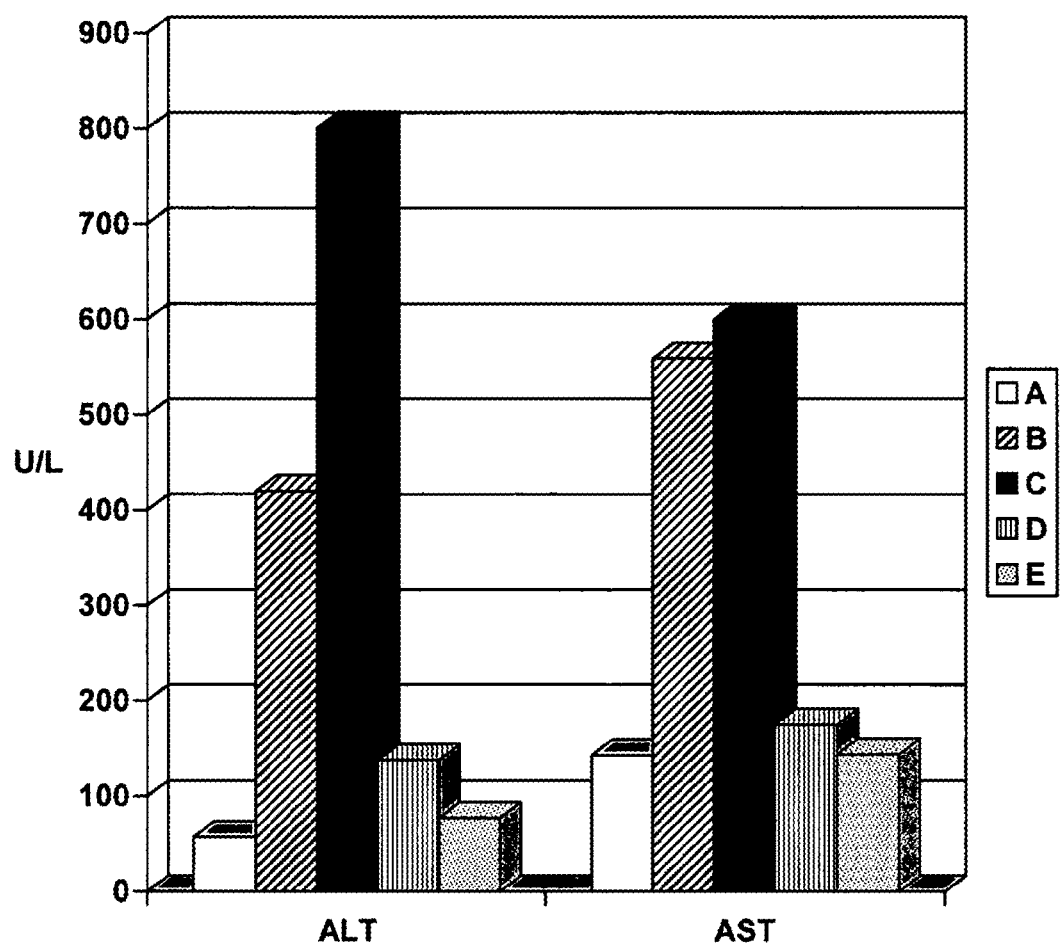
FIG. 4 shows the effect of glucocerebroside on serum ALT and AST levels for mice in Groups A-E shown in Table 1.

Effect of Glucocerebroside on Con A Hepatitis a. Effect of Glucocerebroside on Serum ALT and AST Levels (FIG. 4)

Figure 5:
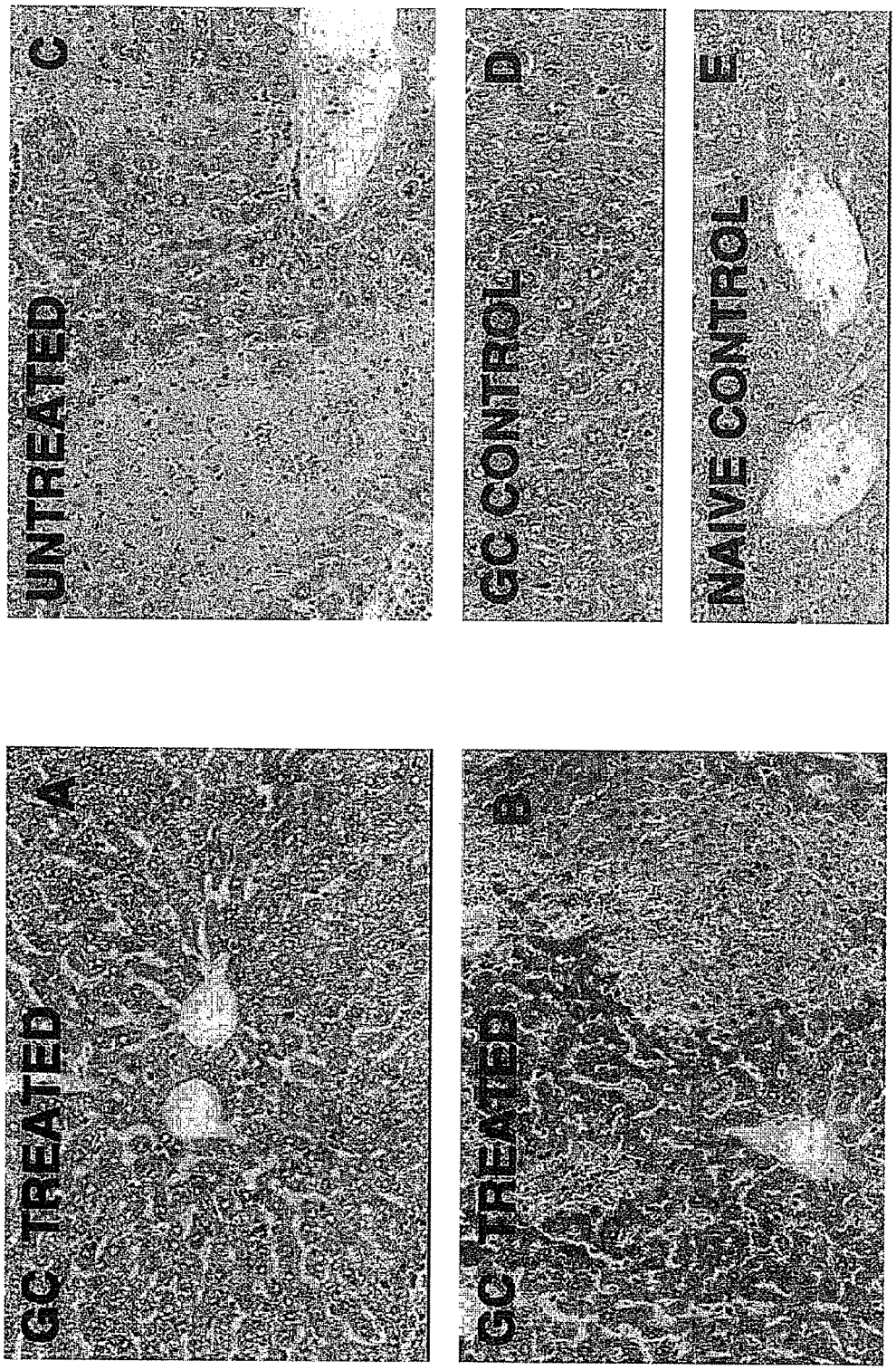
FIG. 5 shows the effect of glucocerebroside on liver histology. Panel A shows results for Group A mice; panel B shows results for Group B mice; panel C shows results for Group C mice; panel D shows results for Group D mice; panel E shows results for Group E mice.

Administration of glucocerebroside led to a marked decrease of serum AST and ALT levels in group A mice, treated by GC prior to ConA administration, compared to group C mice, that did not receive GC (143 IU vs. 600 IU, respectively, for serum AST levels; 57 IU vs. 801 IU, respectively, for serum ALT levels, p<0.05). Serum AST and ALT levels were decreased to a lesser degree in group B animals, that were treated with GC after induction of ConA hepatitis (559 IU, and 420 IU, respectively); the difference between serum AST and ALT levels in group B compared to group C was not statistically significant. Administration of GC to naïve animals (group D) did not lead to a significant change in serum AST or ALT levels (175 IU vs. 144 IU for serum AST and 138 IU vs. 77 IU for serum ALT in groups D and E, respectively; p value 0.17 and 0.07, respectively).

b. Effect of Glucocerebroside on Liver Histology (FIG. 5)

Pathological evidence of liver injury was correlated with serum AST and ALT levels. Histological liver damage was markedly attenuated in group A liver specimens (panel A) in comparison to to group B and C liver specimens (panels B and C), in which massive hepatocyte necrosis was present. Livers of group D mice, that were treated by GC alone (panel D), were identical in appearance to the normal livers of naïve group E animals (panel E).

c. Effect of Glucocerebroside on Serum Cytokine Levels (FIGS. 6-10)

Figure 6:
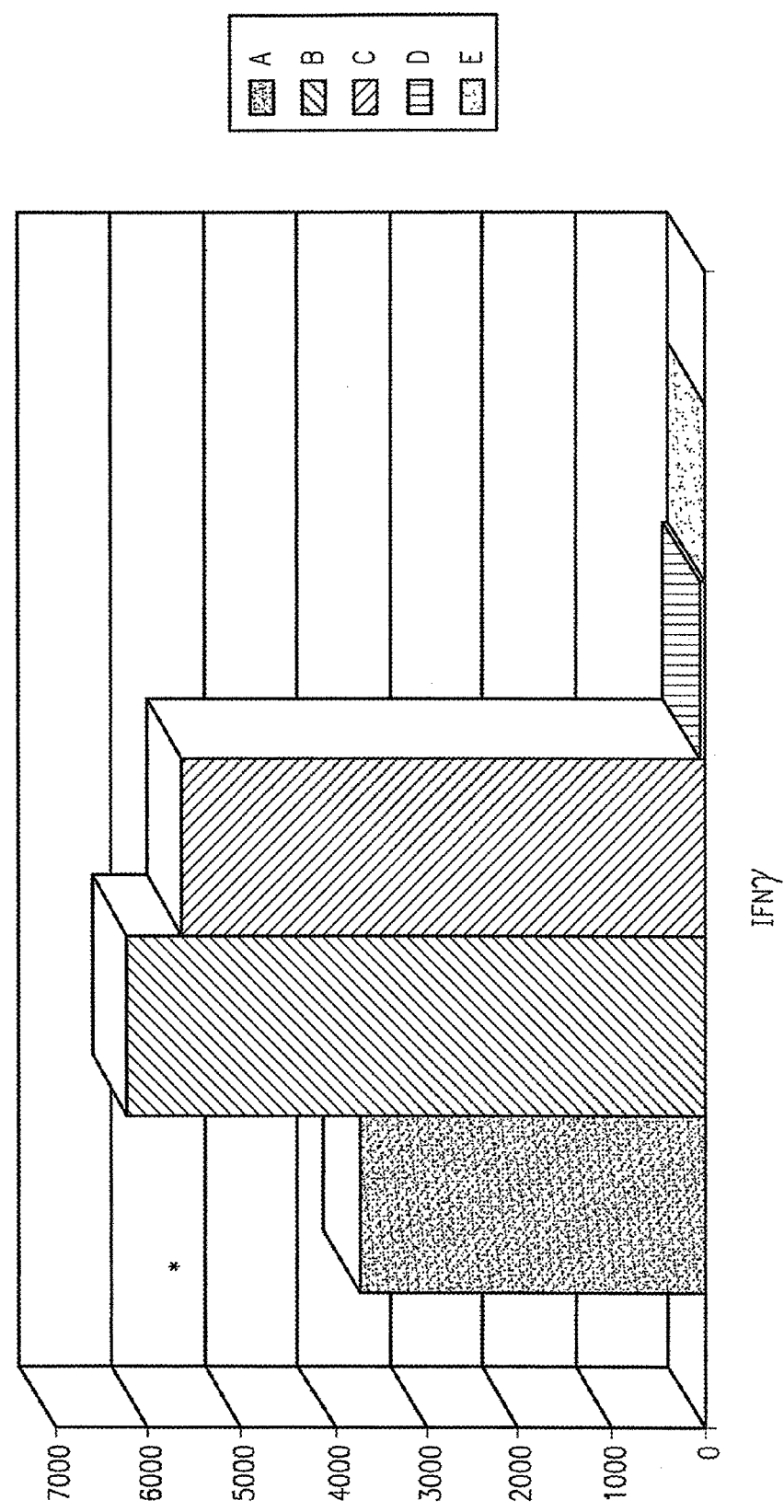
FIG. 6 shows the effect of glucocerebroside on serum IFNγ for mice in Groups A-E shown in Table 1.
Figure 7:
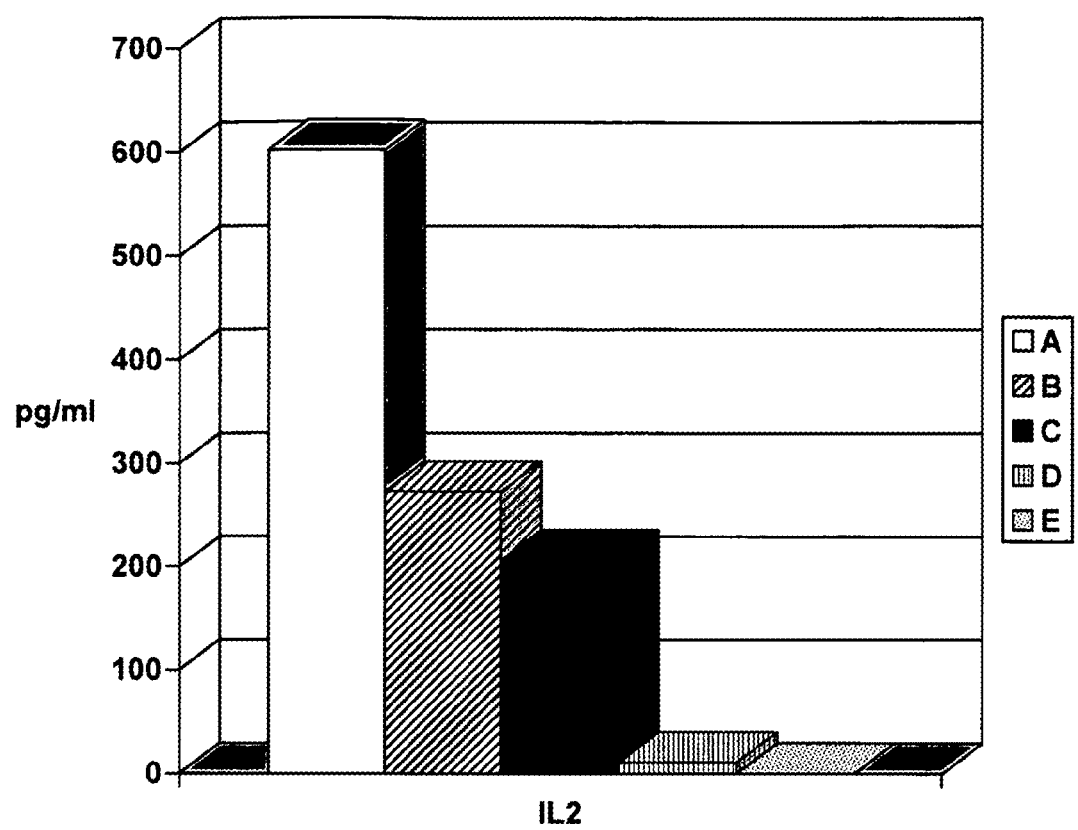
FIG. 7 shows the effect of glucocerebroside on serum IL-2 for mice in Groups A-E shown in Table 1.

Serum IFNγ was significantly lower in group A mice, that were treated by GC two hours prior to ConA administration, compared to group B and C animals (3725 µg/ml in group A vs. 6220 µg/ml and 5620 µg/ml in groups B and C, p<0.05, FIG. 6). Serum IFNγ was negligible in groups D and E (23 µg/ml vs. 0 µg/ml, respectively, p=0.15), which did not receive ConA.

Figure 8:
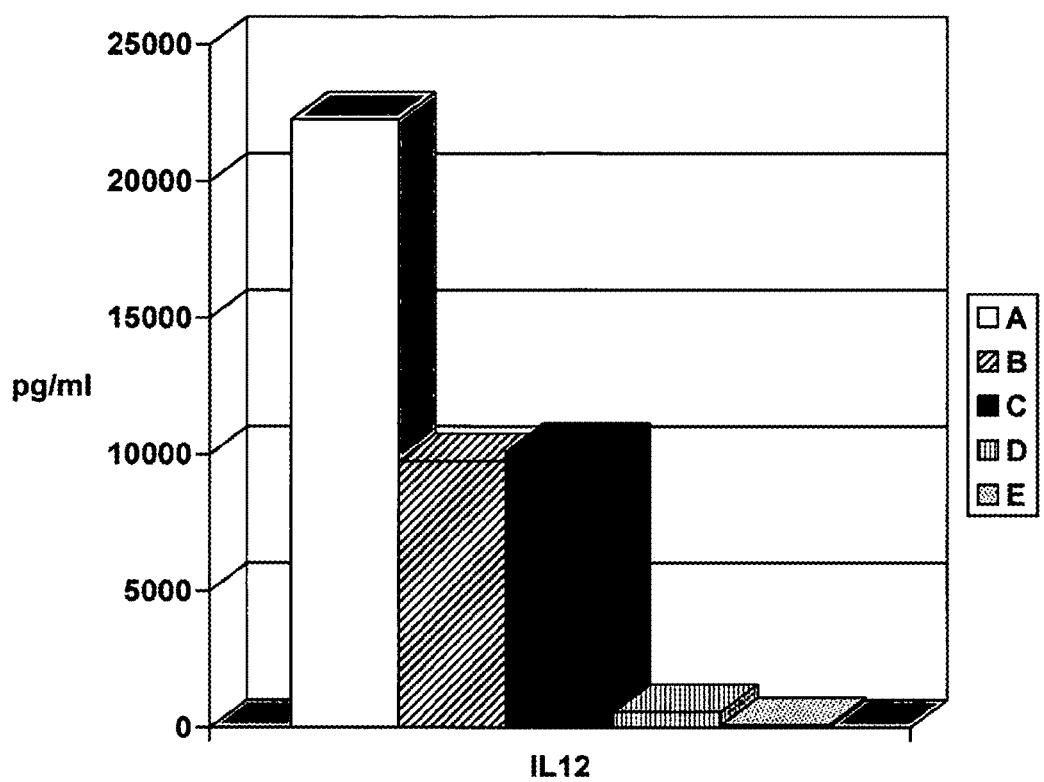
FIG. 8 shows the effect of glucocerebroside on serum IL-12 for mice in Groups A-E shown in Table 1.
Figure 9:
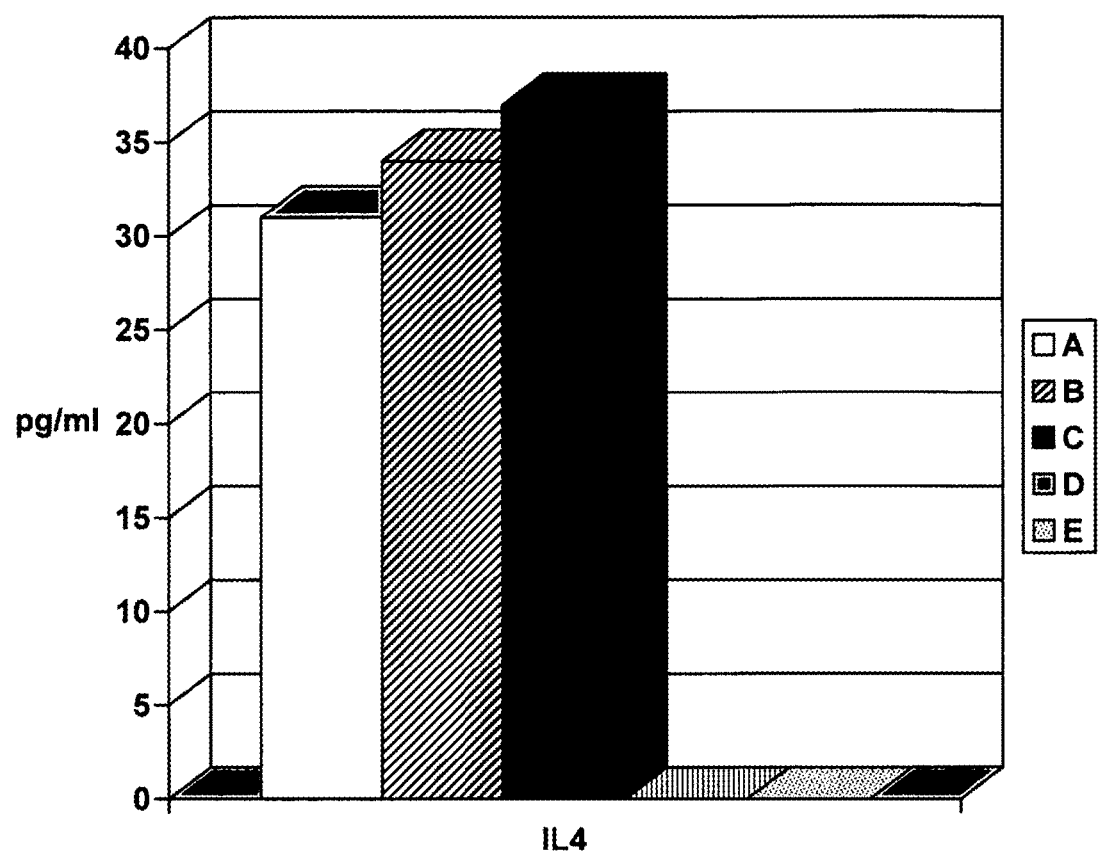
FIG. 9 shows the effect of glucocerebroside on serum IL-4 for mice in Groups A-E shown in Table 1.

Serum IL-2 was significantly higher in GC-treated group A mice compared to untreated group C animals, and did not differ significantly between groups B and C (602 µg/ml vs. 273 µg/ml and 206 µg/ml in groups A, B and C, respectively; p<0.05, FIG. 8). Serum IL-2 was also significantly elevated in non ConA-treated group D mice, that received GC, compared to naïve group E animals (11 pg/ml vs. 0.2 pg/ml, p<0.05).

Serum IL-12 was markedly higher in GC-treated group A mice compared to untreated group C animals, and was similar in groups B and C (22250 pg/ml, 9740 pg/ml and 10100 pg/ml in groups A, B and C, respectively; p<0.05, FIG. 8). Serum IL-12 was also significantly elevated in non ConA-treated group D mice, that received GC, compared to naïve group E animals (573 pg/ml vs. 92 pg/ml, p<0.05).

Serum IL-4 was higher in all ConA treated groups (A-C) compared to non-ConA treated animals (D,E). There was no significant difference between serum IL-4 levels in groups A, B and C (31 pg/ml, 34 pg/ml and 37 pg/ml, respectively, FIG. 9) or in groups D and E (0 pg/ml in both groups).

Figure 10:
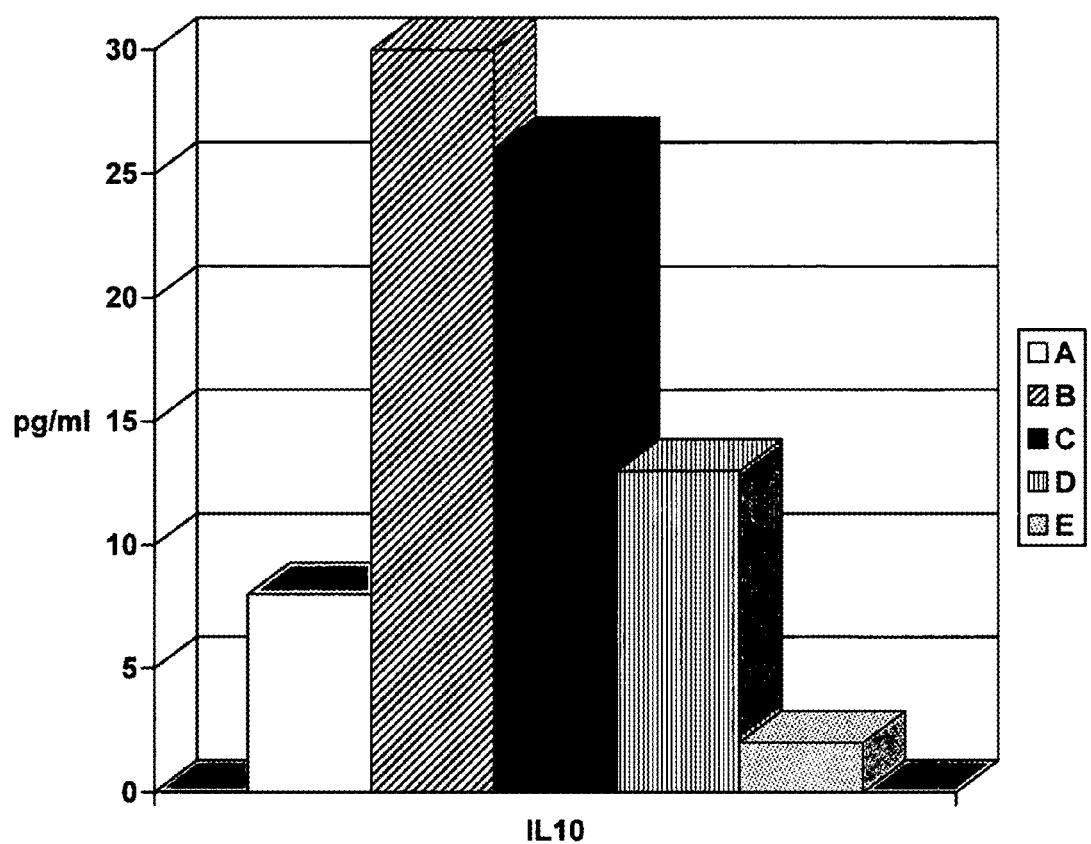
FIG. 10 shows the effect of glucocerebroside on serum IL-10 for mice in Groups A-E shown in Table 1.
Figure 11:
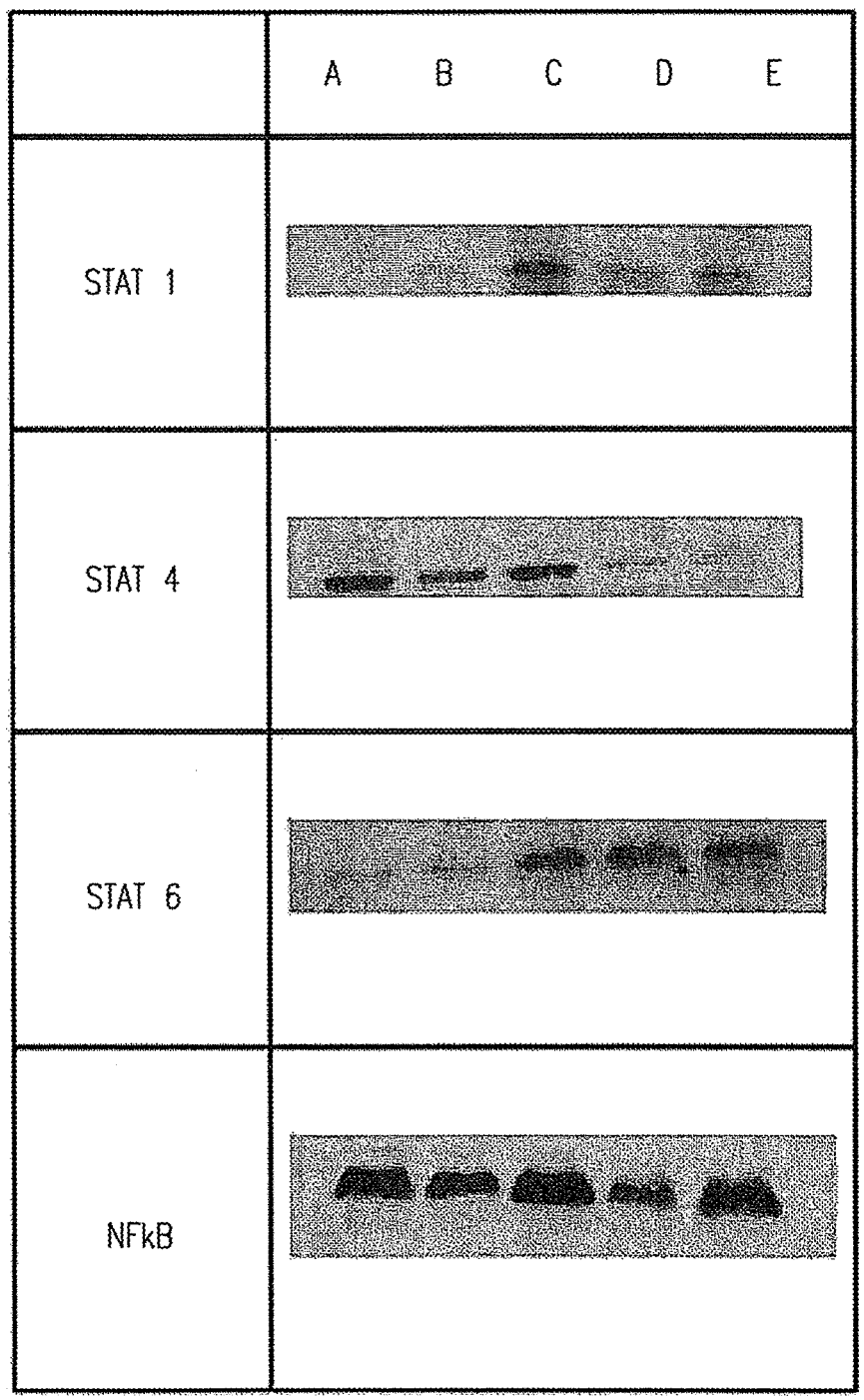
FIG. 11 shows the effect of glucocerebroside on expression of the transcription factors STAT 1,4 and 6 and NFκB for mice in Groups A-E shown in Table 1.

There was a trend towards decreased serum IL-10 in GC-treated group A mice compared to groups B and C (8 pg/ml in group A vs. 30 pg/ml and 26 pg/ml in groups B and C, respectively, FIG. 10) that did not reach statistical significance (p=0.07). Interestingly, in GC-treated naïve mice (group D) a trend towards higher IL-10 levels was observed (13 pg/ml vs. 2.3 pg/ml in groups D and E, respectively) that did not reach statistical significance (p=0.08).

d. Effect of Glucocerebroside on Expression of the Transcription Factors STAT 1,4 and 6 and NFκB (FIG. 11)

Figure 12:
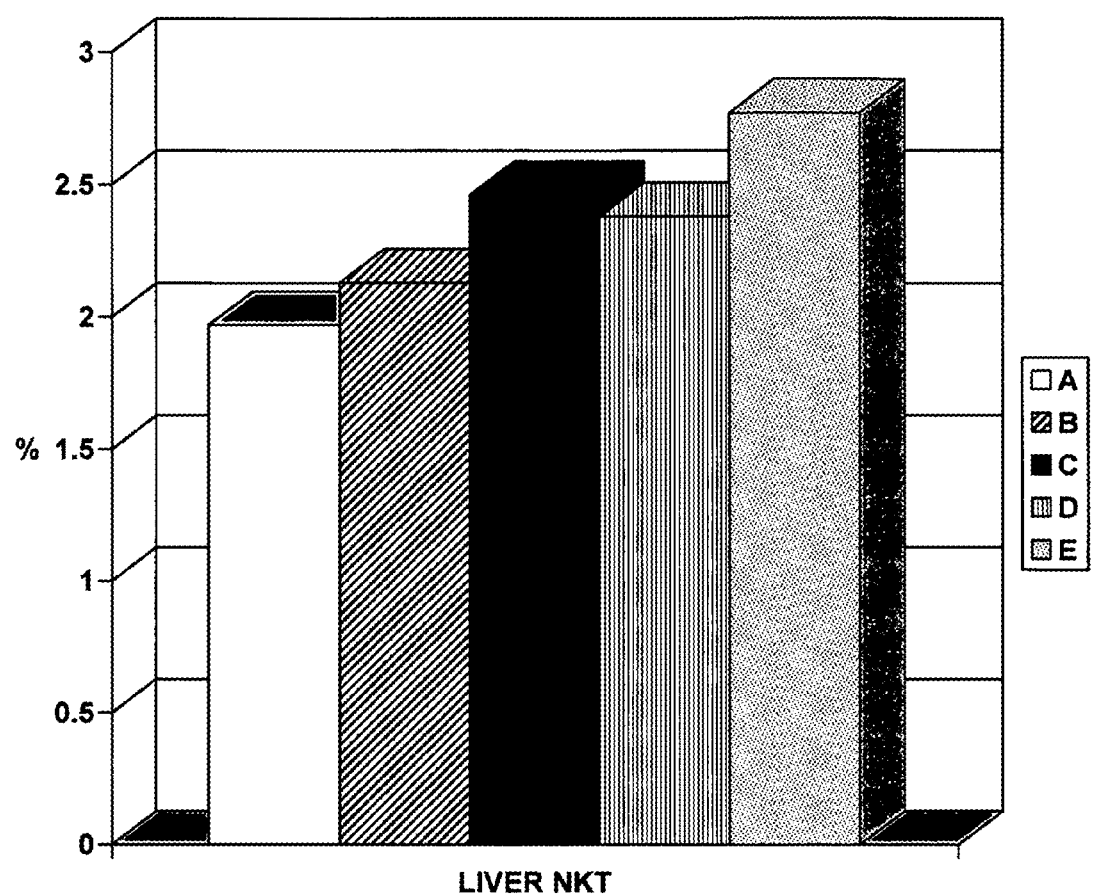
FIG. 12 shows the effect of glucocerebroside on intrahepatic NKT lymphocytes for mice in Groups A-E shown in Table 1.
Figure 13:
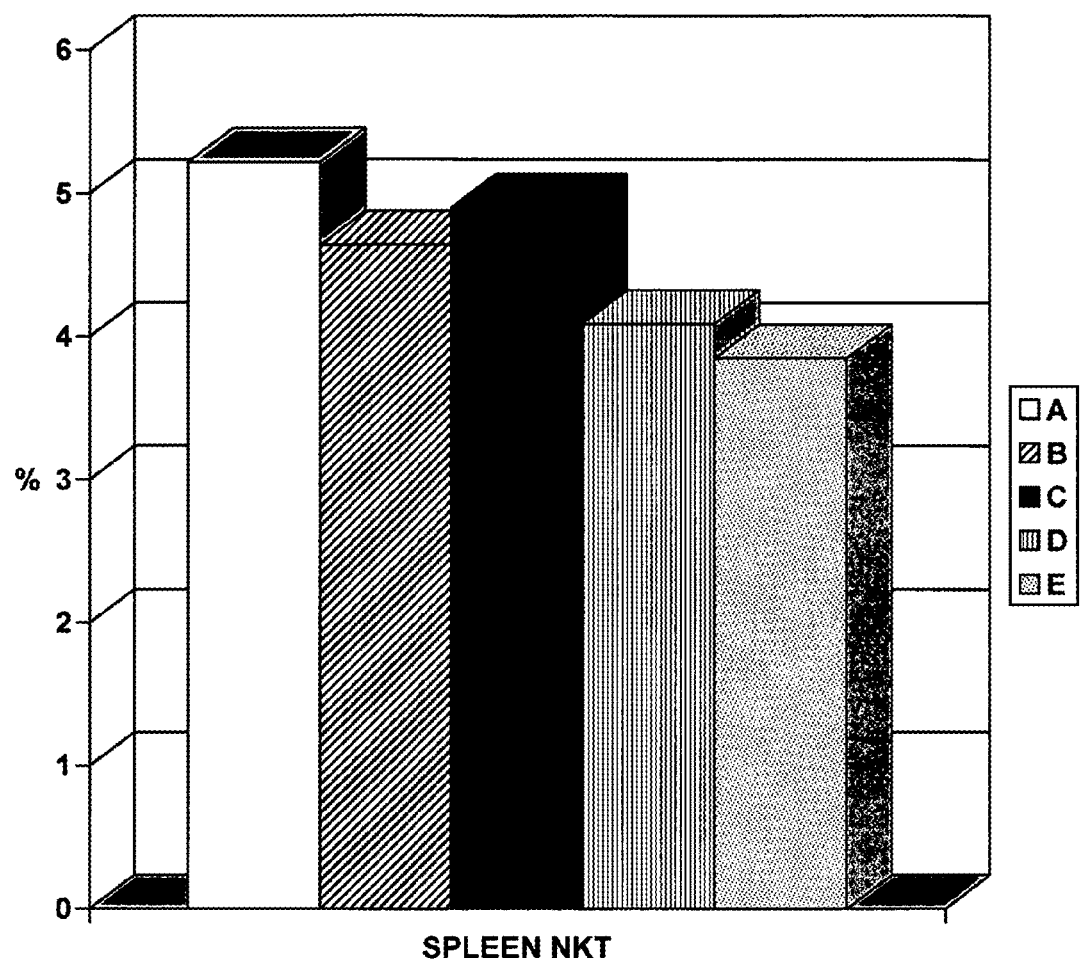
FIG. 13 shows the effect of glucocerebroside on peripheral NKT lymphocytes for mice in Groups A-E shown in Table 1.

Expression of STAT 1, associated with activation of the IFNγ receptor, was decreased in group A (and to a lesser extent—in group B) compared to group C, and in group D compared to group E. Expression of STAT 4, classically associated with activation of the IL-12 receptor, was markedly increased in group A compared to groups B and C, and slightly increased in group D compared to group E. Expression of STAT 6, associated with activation of the IL-4 receptor, was prominently reduced in group A (and to a lesser degree—in group B) compared to group C-E. There was no difference in NFκB expression among the study groups.

e. Effect of Glucocerebroside on Splenic and Intrahepatic NKT Lymphocytes:

The effect of glucocerebroside on the number of NKT cells in the liver and spleen was examined. Among ConA-treated groups, administration of GC led to a 24% decrease in the intrahepatic lymphocyte number in group A, that was treated by GC two hours prior to ConA administration, compared to group C, that did not receive GC treatment (2.17% vs. 2.87% NKT lymphocytes in groups A and C, respectively, p<0.05, FIG. 12). An increased NKT cell number was observed in group B (3.28%), that was treated with GC after ConA administration. Administration of glucocerebroside to naïve mice (group D) led to a slight reduction of the intrahepatic NKT cell number (2.38% vs. 2.51% in groups D and E, respectively) that was not statistically significant (p=0.22). In the spleen, a small, statistically insignificant increase in the NKT lymphocyte number was observed in GC-treated group A mice compared to group C animals (5.22% vs. 4.90%, respectively), and in group D mice compared to naïve group E controls (4.09% vs. 3.85%, respectively) (FIG. 13).

Discussion

In vivo, administration of glucocerebroside two hours prior to injection of ConA, led to marked alleviation of ConA-induced hepatitis, reflected by significantly decreased serum aminotransferase levels and markedly attenuated liver necrosis in GC-treated mice. Although serum transaminases were somewhat reduced in mice treated by glucocerebroside two hours after ConA administration (group B), histological damage and most of the immunological parameters were indistinguishable from those in untreated animals. It is noteworthy that administration of GC to naive animals did not cause hepatitis; this contrasts with the administration of αGalCer, which leads to severe hepatitis that shares many features with ConA induced hepatitis, limiting its therapeutic application (Osman et al., 2000, Eur J Immunol 30:1919)

Amelioration of ConA-induced liver damage was associated with decreased serum IFNγ ☐levels and reduced expression of the transcription factor STAT1, which is associated with activation of the IFNγ ☐☐ receptor☐☐ Together with TNFα, IFNγ, is considered to have a key role in the pathogenesis of ConA-induced hepatitis (Gantner et al., 1995, Hepatology 21: 190-8; Kü̇sters et al., 1996, Gastroenterology 111: 462-71; Nishimura et al., 1999, J Immunol 162: 6503-09 and Nicoletti et al., 2000, Cytokine 12: 315-23). In addition, the IFNγ-inducing cytokines, IL-12 and IL18, and macrophage inflammatory protein-2 (MIP-2) contribute to the liver injury in this model (Nicoletti et al., 2000, Hepatology 32: 728-33 and Faggioni et al., 2000, Proc Natl Acad Sci USA 97: 2367-72), whereas IL6, IL11 and IL-10 may have a protective role (Mizuhara et al., 1994, J Exp Med. 1994; 179: 1529-37 and Di Marco et al., 1999, Autoimmunity 31:75-83). While it was previously suggested that IL-4 may inhibit acute liver damage and TNFα production in this model (Kato et al., 2000, Am J Pathol 157: 297-302), recent studies have shown that anti-IL-4 antibody prevents ConA hepatitis (Toyabe et al., 1997, J Immunol. 159: 1537-42) and that Vα14 NKT cells enriched from spleens of IL-4-/- mice and adoptively transferred into Vα14-deficient knockout mice fail to restore susceptibility to ConA, suggesting that IL-4 produced by NKT cells is required for the induction of ConA hepatitis (Kaneko et al., 2000, J Exp Med 191: 105-14). Serum IL-4 did not differ significantly among the ConA treated groups in the present study; however, STAT6 expression, associated with IL-4 receptor activation, was reduced in group A compared to group C, implying reduced IL-4 activity in animals in which amelioration of ConA-induced hepatitis occurred.

The beneficial effect of GC in ConA-induced hepatitis was associated with a 20% decrease of the intrahepatic NKT cell number; notably, a similar effect was observed in GC-treated mice that were not exposed to Con-A (group D). At the same time, a slightly increased peripheral NKT cell number was observed in GC-treated groups. One possible explanation for this finding is re-distribution of NKT cells, that is—expulsion of these cells from the liver to the periphery, thus alleviating NKT-mediated liver damage. Other possible explanations for the decreased number of intrahepatic NKT cells in this study may include glucocerebroside-mediated inhibition of NKT cell proliferation, glucocerebroside-mediated apoptosis and altered subpopulations of NKT lymphocytes. These mechanisms may also underlie the amelioration of ConA-induced hepatitis observed in this study, although a role for non-NKT cell-related mechanisms cannot be excluded.

In vitro, inhibition of NKT cell proliferation was shown to be dependent on the presence of dendritic cells. This supports a requirement for antigen presentation for the inhibitory effect of glucocerebroside, rather than a direct effect of glucocerebroside on NKT cells. One possible explanation for the inhibitory effect of GC observed in the present study is displacement of a yet-uncharacterized natural activating ligand from the CD1d molecule. Binding of glycolipids to CD1d is mediated by anchoring of their lipid tail to the hydrophobic pockets of the CD1d antigen-binding groove [45]. Occupation of the CD1d molecule by the ceramide tail of GC, which does not activate NKT lymphocytes, may competitively inhibit binding and presentation of activating ligands, in a similar manner to that recently demonstrated for CD1b, another glycolipid-presenting molecule [46]. It was recently demonstrated that β-galactosylceramide binds to CD1d without activating NKT cells [47]. Interestingly, the mere presence of dendritic cells was also found to decrease NKT lymphocyte proliferation. As dendritic cells may constitutively express CD1d-bound ligands that could influence NKT cell activation, this effect may have been CD1d-mediated. Alternatively, the inhibitory effect of dendritic cells on NKT lymphocyte proliferation may have been unrelated to CD1d-mediated interactions. In a similar manner, the further inhibition of NKT cell proliferation by glucocerebroside could be CD1d-related or unrelated.

Glucocerebroside-induced apoptosis may be mediated by glucocerebroside itself or by altered levels of other compounds in its metabolic pathway, such as ceramide, which has a well-characterized pro-apoptotic effect. Apoptosis of effector cells that mediate ConA-induced liver damage can be expected to ameliorate ConA-induced hepatic injury.

The decreased number of intrahepatic NKT cells and amelioration of ConA-induced hepatitis observed in this study may have resulted from altered proportions of subpopulations of NKT lymphocytes. NKT lymphocytes include subpopulations that are phenotypically and functionally diverse (Emoto et al., 2003, Trends Immunol 24: 364-9). The CD3+DX5+ NKT cells identified in this study are one population of NKT cells, made up mostly of "classical" Vα14+ NKT lymphocytes; as other surrogate markers for identification of NKT cells were not used, the decreased number of intrahepatic NKT lymphocytes may reflect a relative reduction in the proportion of this subpopulation of NKT cells, rather than a truly lower total NKT lymphocyte number.

It is possible that the decreased intrahepatic NKT cell number observed in this study resulted from hastening of activation-induced apoptosis of NKT cells by GC (i.e. more vigorous activation of these cells). While GC may induce an altered NKT lymphocyte response that is not strictly inhibitory and may differ in various microenvironments and disease states, possibly influenced by the presence of soluble elements and costimulatory molecules, previous data and the complete absence of resultant liver damage in GC-treated animals argues against the possibility that the in vitro inhibition of NKT cell proliferation and in vivo disappearance of intrahepatic NKT cells in this study were activation-induced.

Glucocerebroside is normally a constituent of cell membranes; its levels are relatively high in reticuloendothelial tissues (i.e. liver, spleen and bone marrow) involved in metabolism of senescent blood cells. The relative distribution of radiolabeled GC observed in this study is not in line with straightforward incorporation into cellular membranes or scavenging by reticuloendothelial cells. This notion is supported by the observed accummulation of GC in the small bowel and colon following both oral or intraperitoneal administration. Although hepatic accummulation of GC may have partly resulted from metabolism and excretion of GC by the liver, the observed clinical effect supports an additional role for GC in this organ.

The amounts of GC normally present in the body are vastly greater than those administered in this study. It was previously shown that the average splenic GC content is 0.090±0.047 mg per gram wet tissue, and 19.9±4.2 mg per gram wet tissue, in normal subjects and patients with Gaucher's disease, respectively (Kuske et al., 1972, J Lab Clin Med 80: 523-9). The observed clinical effect in the present study may have resulted from an altered mode of administration, the presence of "free" rather than bound glucocerebroside, or a different structure of the ceramide tail of naturally occurring murine glucocerebroside, in comparison to soy-derived glucocerebroside. In contrast to mammalian glucocerebroside, which has a single trans double bond at position 4, the soy-derived glucocerebroside used in this study has 2 double bonds, at positions 4 and 8 (65% trans, 35% cis) (Sullard et al., 2000, J Mass Spectrom 35: 347-53). While it could be argued that alleviation of ConA hepatitis by GC may have resulted from direct binding and neutralization of ConA, this possibility appears unlikely in view of the molar ratio of GC:ConA.

In summary, the in vitro and in vivo results of this study suggest that soy-derived glucocerebroside, an easily obtainable, naturally occurring glycolipid, is an immune-modulator agent that inhibits NKT lymphocyte activity. Glucocerebroside may have a future role in the treatment of autoimmune hepatitis and other immune-mediated disorders, particularly those in which NKT lymphocytes contribute to disease pathogenesis.

II. Glucocerebroside Treatment of Non-Alcoholic Steatohepatitis
Methods
Animals 8-week old male ob/ob mice were purchased from Jackson laboratories (Bar Harbor, Me.). Animals were housed in laminar flow hoods in sterilized cages and given irradiated food and sterile acidified water. Animal experiments were carried out in accordance with the guidelines of the Hebrew University-Hadassah Institutional Committee for care and use of laboratory animals and with the committee's approval.

Preparation of Glycolipids

Glucocerebroside was purchased from Avanti Polar Lipids (Alabaster, Ala.) and dissolved in ethanol. Emulsification in PBS was then performed.

Experimental Groups

Four groups of mice were studied. Ob/Ob mice (groups A and B, N=12 per group) and lean C57BL mice (groups C and D, N=12/group) were treated with daily injections of GC (1.5 pg IP, groups A and C) or PBS (100 μl, groups B and D) for 8 weeks.

Followup Parameters

Mice were followed by serial body weight measurements and glucose tolerance tests, determination of serum ALT and AST and triglyceride levels, and assessment of liver size and hepatic fat content by magnetic resonance imaging (MRI) and histological examination.

Glucose Tolerance Test

Mice underwent a glucose tolerance test on day 60. Glucose was administered orally (1 g per kg). Serum glucose measurements were performed on tail-vein blood every fifteen minutes for three hours. Glucose levels were measured by a standard glucometer.

MRI Hepatic Fat Content Measurement

Mice underwent magnetic resonance imaging (MRI) on day 60. Liver size was assessed, and hepatic fat content was measured by a double-echo chemical shift gradient-echo sequence technique, that provides in-phase and out-of-phase images in a single acquisition for assessment and quantification of liver fat. T1-weighted out-of-phase MR imaging is sensitive for detection of relatively small proportions of tissue fat (Mitchell et al., 1991, Invest Radiol 26:1041-10522 and Namimoto et al., 2001, Radiology 218(3):642-646).

MRI images were acquired by a 1.5-T system (Sigma LX;GE, Milwaukee, USA). Double-echo MR imaging was performed with a repetition time (TR) of 125 msec, double echo times (TEs) of 4 and 6.5 msec, and a flip angle of 80°. Imaging parameters included section thickness of 3 mm, a 13-cm field of view and a 256*160 matrix. Axial and coronal images were obtained. Signal intensity (SI) changes between in-phase and out of phase images were computed. The SI index was calculated as follows: SI index (SII)=(Slip-Slop)/Slip (Slip=in-phase SI; Slop=out of phase SI). Low SI index values indicate a smaller amount of tissue fat. An MRI fatty liver index (MFI=liver area*SII) was calculated for each animal.

Triglyceride Measurement

On day 60, serum triglyceride levels were measured using a spectrophotometer (Cobas DP-25P).

Liver Steatohepatitis Score

A liver segment from each mouse was fixed in 10% formaldehyde and embedded in paraffin for histological analysis. Five sections (5 μm) were stained with hematoxylin/eosin and reviewed by two pathologists in a blinded fashion.

Measurement of Serum Cytokines

Serum IFNγ, IL-10 and IL-4 levels were measured by a "sandwich" ELISA method using Genzyme Diagnostic kits (Genzyme Diagnostics, MA, USA), according to manufacturer's instructions.

Isolation of Splenic and Hepatic Lymphocytes for Determination of T Cell Subpopulations Mice were sacrificed on day 60 of the experiment. Splenic lymphocytes and NKT cells were isolated and red blood cells removed as previously described (Trop et al., 2002, J Clin Immunol 22: 270-80). Intrahepatic lymphocytes were isolated as follows: After cutting the inferior vena cava above the diaphragm, the liver was flushed with cold PBS until it become pale, followed by removal of connective tissue and gall bladder. Livers and spleens were crushed through a stainless mesh (size 60, Sigma Chemical Co., St. Louis Mo.). The cell suspension was placed in a 50 ml tube for 3 minutes and washed twice in cold PBS (1,250×rpm for 10 minutes). Cells were re-suspended in PBS, cell suspension was placed through a nylon mesh presoaked in PBS, and unbound cells were collected. For liver and spleen lymphocyte isolation, 20 ml of histopague 1077 (Sigma Diagnostics, St. Louis, Mo.) were placed under the cells. The tube was centrifuged at 1,640×rpm for 15 minutes in room temperature. Cells at the interface were collected, diluted in a 50-ml tube, and washed twice with ice-cold PBS (1,250×rpm for 10 minutes). Approximately $1 \times 10^6$ cells/mouse liver were recovered. The viability by trypan blue staining was above 95%.

Flow Cytometry Analysis for Determination of CD4, CD8, and NKT Lymphocyte Populations Following lymphocyte isolation, triplicates of $2-5 \times 10^5$ cells/500 μl PBS were placed in Falcon 2052 tubes, incubated with 4 ml of 1% BSA for 10 minutes, and centrifuged at 1400×rpm for 5 minutes. Cells were resuspended in 10 μl FCS with 1:20 FITC-anti mouse CD3 antibody, 1:20 PE-anti mouse CD4 antibody, 1:20 APC-anti mouse CD8 antibody, or 1:20 FITC-anti mouse NK1.1 antibody (NKR-P1C, Pharmingen, USA), and mixed every 10 minutes for 30 minutes. Cells were washed twice in 1% BSA, and kept at 4° C. until reading. For the control group, only 5 μl of 1 BSA was added. Analytical cell sorting was performed on $1 \times 10^4$ cells from each group with a fluorescence-activated cell sorter (FACSTAR plus, Becton Dickinson). Only live cells were counted, and background fluorescence from non-antibody-treated lymphocytes was subtracted. Gates were set on forward- and side-scatters to exclude dead cells and red blood cells. Data was analyzed by the Consort 30 two-color contour plot (Becton Dickinson, Oxnard, Calif.) or CELL-Quest programs.

Statistical Analysis:

The Student t-test was used for data analysis; $p<0.05$ was considered statistically significant.

Results:

Effect of Glucocerebroside on Body Weight

Figure 14:
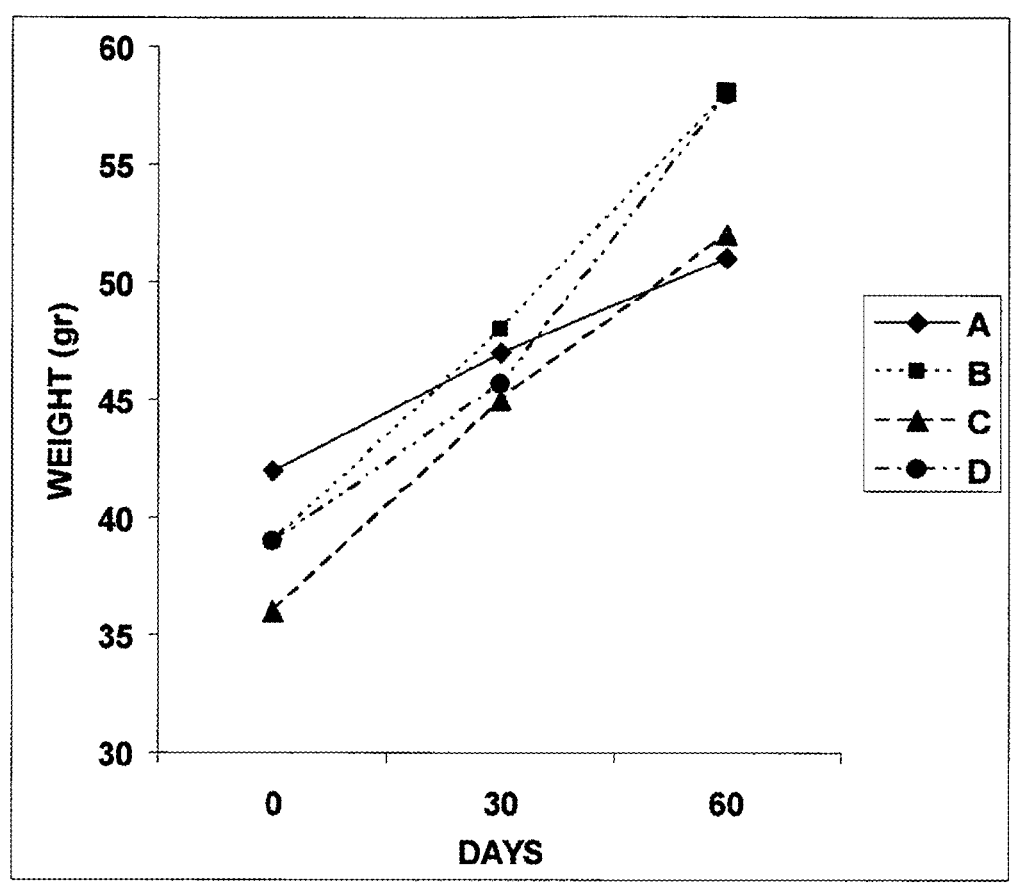
FIG. 14 shows the effect of glucocerebroside on body weight in A: ob/ob mice treated with GC; B: untreated ob/ob mice; C: lean mice treated with GC and D: untreated lean mice.

The increase in body weight during the study period was significantly attenuated in leptin-deficient ob/ob mice that were treated by glucocerebroside (group A) compared to control ob/ob animals (group B). There was a 21.6% increase of body weight in group A, compared to a 48.4% increase of body weight in group B ($p<0.05$, FIG. 14). Administration of glucocerebroside to lean C57BL mice did not affect the degree of body weight gain. Mice in groups C and D gained 41.8% and 42.2% of their initial weight, respectively.

Effect of Glucocerebroside on Liver Size and Hepatic Fat Content

Figure 15:
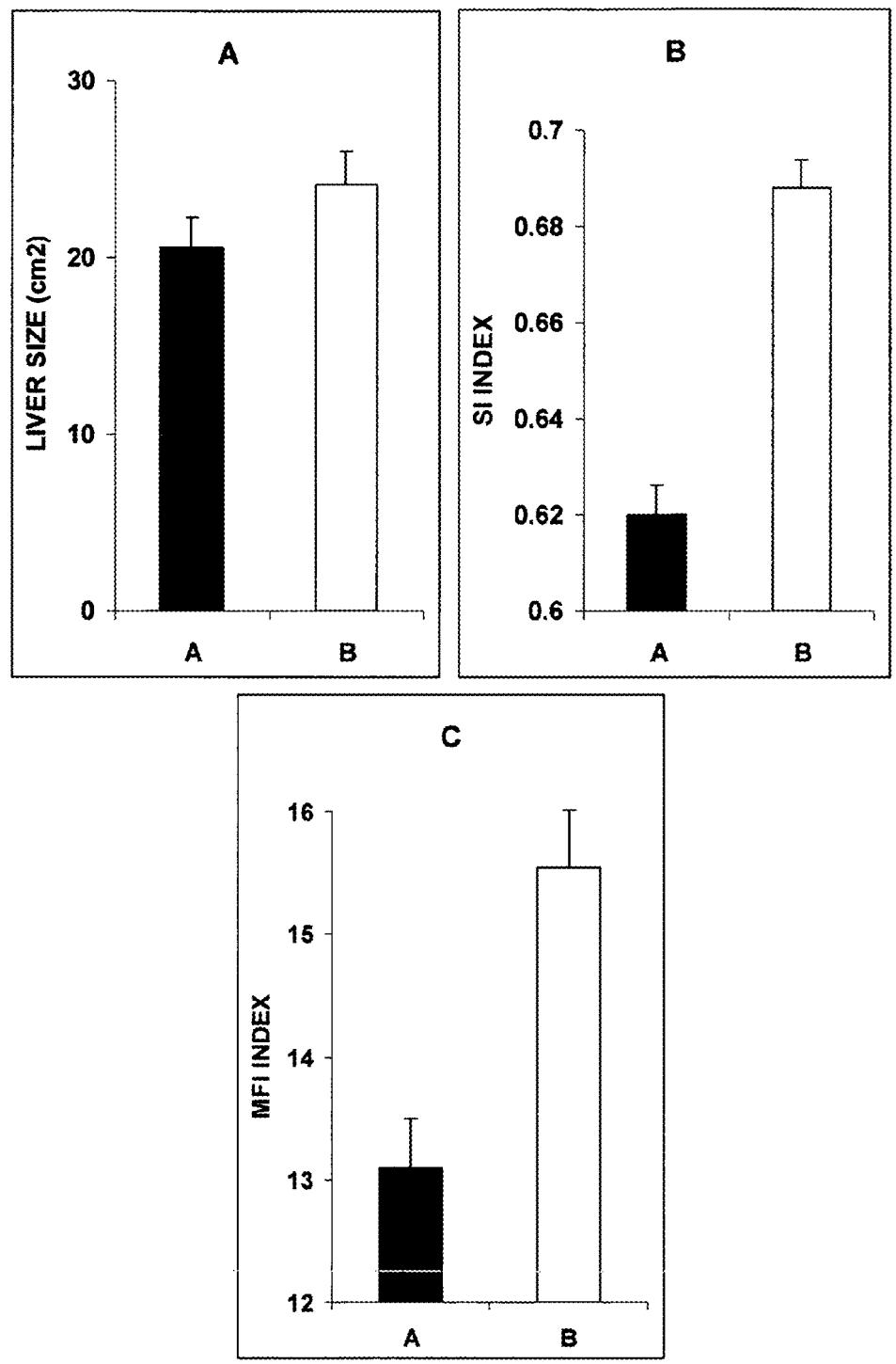
FIG. 15 shows the effect of glucocerebroside on liver size (FIG. 15A), SI index (FIG. 15B) and hepatic fat content (MFI Index) (FIG. 15C) in A: ob/ob mice treated with GC and B: untreated ob/ob mice.

Livers of ob/ob mice that were treated by glucocerebroside (group A) were significantly smaller than livers of untreated control ob/ob mice (group B; 20.63 cm$^2$ vs. 24.12 cm$^2$, respectively, $p<0.05$). Glucocerebroside did not affect liver size in lean C57BL mice (10.7 cm$^2$ and 11.75 cm$^2$ in groups C and D, respectively, FIG. 15A). There was a 10.9% decrease in the hepatic SI index in the glucocerebroside-treated ob/ob group compared to control ob/ob mice (SI index 0.620 vs. 0.688 in groups A and B, respectively, $p<0.05$, FIG. 15B, FIG. 16), indicating a significant reduction in the hepatic fat content. As both the liver area and the SI index are correlated with the degree of hepatic fat, their product, MFI (MRI fatty liver index), was calculated to increase the accuracy in detecting a difference between the groups. There was an 18.7% reduction of the MFI in treated (group A) ob/ob mice compared to untreated ob/ob controls (MFI 13.1 vs. 15.55 in groups A and B, respectively, $p>0.05$, respectively). Glucocerebroside treatment also resulted in marked reduction of the hepatic fat content in lean C57BL mice. The SI index was 0.1 in glucocerebroside-treated group C mice compared to 0.18 in untreated group D controls, a reduction of 80% in the intrahepatic fat content. The MFI index decreased from 1.92 to 1.17 in groups D and C, respectively ($p<0.05$, FIG. 15C).

Effect of Glucocerebroside on Liver Histology

Histological examination of livers of glucocerebroside-treated ob/ob mice (group A) compared to control ob/ob mice (group B) revealed a shift from a mixed micro and macrovesicular steatosis pattern in control mice to a mainly microvesicular pattern in glucocerebroside-treated ob/ob animals (FIG. 17).

Effect of Glucocerebroside on Serum Triglyceride Levels

The serum triglyceride level was significantly lower in glucocerebroside-treated ob/ob mice compared to control ob/ob mice (1.57 mmol/l vs. 2.29 mmol/l in groups A and B, respectively). Serum triglyceride levels also decreased in lean C57BL mice (1.31 mmol/l vs. 1.56 mmol/l in glucocerebroside treated vs. untreated animals, respectively).

Effect of Glucocerebroside on Glucose Tolerance

The glucose tolerance test (GTT) was markedly abnormal in control ob/ob mice (339 mg/dl at 1 hour in group B, FIG. 18). In contrast, glucocerebroside-treated ob/ob mice had an almost normal glucose tolerance curve throughout the three-hour test (glucose level 153 mg/dl at 1 hour, $p<0.05$).

Effect of Glucocerebroside on Serum Liver Enzymes

The serum AST and ALT levels did not differ significantly among the groups on day 60.

Effect of Glucocerebroside on Intrahepatic and Intrasplenic Lymphocyte Subsets:

FACS analysis of peripheral and intrahepatic lymphocytes revealed a 1.6 timefold increase of the peripheral/intrahepatic NKT lymphocyte ratio in glucocerebroside-treated ob/ob mice compared to controls (peripheral/intrahepatic NKT lymphocyte ratio 3.46 vs. 2.13 in group A and B, respectively, $P<0.05$, FIG. 19); this ratio increased 3.73 timefold in glucocerebroside-treated lean C57BL mice compared to control lean C57BL mice (peripheral/intrahepatic NKT lymphocyte ratio 2.13 vs. 0.57 in groups C and D, respectively, $p<0.05$, FIG. 19). The intrahepatic CD4+/CD8+ lymphocyte ratio was significantly increased in the GC treated group compared to non treated controls (4.09 vs. 2.18 in group A and B, respectively, $P<0.05$). This change was specific to the liver and was not accompanied by a similar change in the peripheral CD4/CD8 ratio (1.53 vs. 1.33 in group A and B, respectively). Thus, the peripheral to intrahepatic CD4/CD8 ratio increased 1.64 timefold in GC treated mice (0.61 vs. 0.37 in group A and B, respectively, P<0.05), suggesting increased intrahepatic CD8 lymphocyte trapping.

Effect of Adoptive Transfer of NKT Lymphocytes on Serum Cytokine Levels:

A 33% decrease of the serum IFNγ level (6.5 pg/ml vs. 9.75 pg/ml in groups A and B, respectively) and a 2.6 timefold increase of the serum IL-10 level (140 pg/ml vs. 53 pg/ml in groups A and B, respectively, p<0.05) were noted in glucocerebroside-treated ob/ob mice compared to control ob/ob mice. The serum IL-4 level did not differ among these groups (FIG. 20). Glucocerebroside did not affect the serum cytokine levels in lean C57BL mice.

Discussion

Administration of glucocerebroside alleviated hepatic steatosis and the metabolic syndrome in leptin-deficient ob/ob mice. In treated mice, less weight gain, lower serum triglyceride levels, almost normal glucose tolerance curves and significantly reduced liver size and liver fat content were observed. Glucocerebroside-treated ob/ob mice had an altered immunological profile, including an increased peripheral/intrahepatic NKT lymphocyte ratio and increased CD8+ T lymphocyte trapping.

The concomitant improvement in steatosis and glucose intolerance that was observed in this study following administration of glucocerebroside reinforces the concept of a close interaction between steatosis and the metabolic syndrome in NASH (Koteish et al., 2001, Seminars in Liver Disease 21:89-104). Glucocerebroside had an impressive effect on glucose tolerance, that was comparable to that observed for currently available drugs, without causing hypoglycemia. The effect of glucocerebroside on body weight differed in animals with steatosis compared to lean controls, suggesting that the mechanism of weight loss was related to a common pathogenic process from which the various derangements characteristic of the metabolic syndrome arise. In contrast, the similar effect of glucocerebroside on the hepatic fat content and serum triglyceride levels in ob/ob and lean C57BL mice, suggests that the metabolic syndrome may be the result of several pathogenic mechanisms, which can be manipulated separately.

In the present study, the beneficial effect of GC was associated with a decreased intra-hepatic NKT cell number. One possible explanation for this finding is re-distribution of NKT cells, that is—expulsion of these cells from the liver to the periphery, thus alleviating NKT-mediated liver damage. Other possible explanations for the decreased number of intrahepatic NKT cells in this study may include glucocerebroside-mediated inhibition of NKT cell proliferation, glucocerebroside-mediated apoptosis and altered subpopulations of NKT lymphocytes. NKT lymphocytes include subpopulations that are phenotypically and functionally diverse. The CD3+DX5+ NKT cells identified in this study are one population of NKT cells, made up mostly of "classical" Vα14+ NKT lymphocytes; as other surrogate markers for identification of NKT cells were not used, the decreased number of intrahepatic NKT lymphocytes may reflect a relative reduction in the proportion of this subpopulation of NKT cells, rather than a truly lower total NKT lymphocyte number.

Leptin deficient ob/ob mice exhibit a Th2 type immune profile (Koteish et al., 2001, Seminars in Liver Disease 21(1):89-104). In the present study, the beneficial effect of GC was associated with a significant decrease in the serum IFNγ level and a significant increase in the serum IL-10 level, compatible with further skewing of the cytokine profile in a Th2 direction. This finding suggests that in ob/ob mice, the serum cytokine profile per se does not explain the characteristic metabolic derangements.

Despite the remarkable effect of glucocerebroside on hepatic fat content and the metabolic syndrome in ob/ob mice, serum aminotransferase levels did not differ significantly between the study groups. In this study, a therapeutic effect was sought after two months, a relatively short time period. It remains to be determined whether a further reduction in hepatic fat content and an effect on serum aminotransferases would result from a longer treatment regimen. In contrast to the significant MRI findings, no significant regression of hepatic steatosis was observed in histological sections of glucocerebroside-treated ob/ob mice. The significance of the transition from a macrovesicular pattern of steatosis to a microvesicular pattern remains unclear. Interestingly, a similar finding was observed with other immune-modulator interventions that had a beneficial effect in this model (Elinav et al., 2003, Hepatology 38:4 (S1) 110A). It remains to be determined whether administration of glucocerebroside for a longer period of time would result in a more marked histological response.

In summary, the results of this study suggest that glucocerebroside has a remarkable beneficial effect on hepatic steatosis and the metabolic syndrome in ob/ob mice. This effect may be mediated by immune modulation of NKT lymphocytes, supporting a major role for the immune system in the pathogenesis of NASH. The long term implications of administration of glucocerebroside in this model, as well as the effect of other dosing regimens of glucocerebroside for variable time durations, remain be determined.

What is claimed is:

1. A method for treating auto-immune hepatitis in a mammalian subject, comprising:
    administering to a mammalian subject having auto-immune hepatitis a pharmaceutical composition comprising a therapeutically effective amount of a β-glucosylceramide,
    wherein said administration improves the auto-immune hepatitis in said mammalian subject.

2. The method of claim 1, wherein the β-glucosylceramide is soy-derived.

3. The method according to claim 1, wherein said subject is subjected to fasting for a minimum of twelve hours prior to said administration of said β-glucosylceramide.

4. The method of claim 3, wherein the β-glucosylceramide is soy-derived.

5. The method of claim 1, wherein the mammalian subject is a human subject.

6. The method of claim 5, wherein said administering step comprises enteral administration of said β-glucosylceramide.

7. The method of claim 5, wherein said administering step comprises parenteral administration of said β-glucosylceramide.

8. The method of claim 2, wherein the mammalian subject is a human subject.

9. The method of claim 8, wherein said administering step comprises enteral administration of said β-glucosylceramide.

10. The method of claim 8, wherein said administering step comprises parenteral administration of said β-glucosylceramide.

11. The method of claim 3, wherein the mammalian subject is a human subject.

12. The method of claim 11, wherein said administering step comprises enteral administration of said β-glucosylceramide.

13. The method of claim 11, wherein said administering step comprises parenteral administration of said β-glucosylceramide.

14. The method of claim 4, wherein the mammalian subject is a human subject.

15. The method of claim 14, wherein said administering step comprises enteral administration of said β-glucosylceramide.

16. The method of claim 14, wherein said administering step comprises parenteral administration of said β-glucosylceramide.

* * * * *